United States Patent
Enatsu et al.

(10) Patent No.: US 10,624,359 B2
(45) Date of Patent: *Apr. 21, 2020

(54) HIGHLY FUNCTIONAL CELLULOSE COMPOSITE

(71) Applicant: ASAHI KASEI CHEMICALS CORPORATION, Tokyo (JP)

(72) Inventors: Kouichirou Enatsu, Tokyo (JP); Haruko Obata, Tokyo (JP); Naoaki Yamasaki, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 684 days.

This patent is subject to a terminal disclaimer.

(21) Appl. No.: 15/351,749

(22) Filed: Nov. 15, 2016

(65) Prior Publication Data

US 2017/0055540 A1 Mar. 2, 2017

Related U.S. Application Data

(62) Division of application No. 14/237,688, filed as application No. PCT/JP2012/070495 on Aug. 10, 2012, now Pat. No. 10,080,371.

(30) Foreign Application Priority Data

Aug. 11, 2011 (JP) ................................ 2011-176177

(51) Int. Cl.
| | | |
|---|---|---|
| A61K 36/00 | (2006.01) | |
| A23C 3/08 | (2006.01) | |
| A23L 29/262 | (2016.01) | |
| A23L 2/02 | (2006.01) | |
| A23L 2/52 | (2006.01) | |
| A23L 2/62 | (2006.01) | |
| A23F 5/24 | (2006.01) | |
| A23C 9/154 | (2006.01) | |
| A23F 3/16 | (2006.01) | |
| A61K 9/00 | (2006.01) | |
| A61K 47/38 | (2006.01) | |
| C08L 1/02 | (2006.01) | |
| C08L 5/00 | (2006.01) | |
| C09D 7/65 | (2018.01) | |
| A23F 5/14 | (2006.01) | |
| A23G 1/56 | (2006.01) | |
| C08L 1/04 | (2006.01) | |
| C08L 1/28 | (2006.01) | |

(52) U.S. Cl.
CPC .............. *A23C 3/08* (2013.01); *A23C 9/1544* (2013.01); *A23F 3/163* (2013.01); *A23F 5/14* (2013.01); *A23F 5/243* (2013.01); *A23G 1/56* (2013.01); *A23L 2/02* (2013.01); *A23L 2/52* (2013.01); *A23L 2/62* (2013.01); *A23L 29/262* (2016.08); *A61K 9/0095* (2013.01); *A61K 47/38* (2013.01); *C08L 1/02* (2013.01); *C08L 1/04* (2013.01); *C08L 1/286* (2013.01); *C08L 5/00* (2013.01); *C09D 7/65* (2018.01); *A23V 2002/00* (2013.01); *C08L 2203/02* (2013.01); *C08L 2205/02* (2013.01)

(58) Field of Classification Search
CPC ........ A61K 36/00; A61K 36/02; A61K 36/03; A61K 36/04; A61K 36/05
USPC ........................................ 424/195.17, 195.18
See application file for complete search history.

(56) References Cited

U.S. PATENT DOCUMENTS

| | | | | |
|---|---|---|---|---|
| 3,761,465 A | * | 9/1973 | Callihan | ................. C08B 11/12 536/43 |
| 5,674,664 A | | 10/1997 | Tanikawa | |
| 6,087,135 A | | 7/2000 | Kierulff | |
| 2005/0272836 A1 | | 12/2005 | Yaginuma | |
| 2013/0022730 A1 | | 1/2013 | Obata et al. | |

FOREIGN PATENT DOCUMENTS

| | | | |
|---|---|---|---|
| CN | 1512840 A | 7/2004 | |
| CN | 102834447 | 12/2012 | |
| EP | 0643302 A1 * | 3/1995 | ............. G01N 30/88 |
| EP | 1070740 | 1/2001 | |
| GB | 1190112 | 4/1970 | |
| JP | 40-12174 | 6/1940 | |
| JP | 05-255538 | 10/1993 | |
| JP | 09-3243 | 1/1997 | |
| JP | 2002-300854 | 10/2002 | |
| JP | 2005-176749 | 7/2005 | |
| JP | 2005176749 A * | 7/2005 | |

(Continued)

OTHER PUBLICATIONS

International Search Report for PCT/JP2012/070495, dated Sep. 11, 2012.

(Continued)

*Primary Examiner* — Michael Barker
*Assistant Examiner* — Deborah A Davis
(74) *Attorney, Agent, or Firm* — Greenblum & Bernstein, P.L.C.

(57) ABSTRACT

A method for producing a cellulose composite containing cellulose and a polysaccharide, wherein a median size of colloidal cellulose composites contained in the cellulose composite as measured by a dynamic light scattering method is 0.85 μm or more, the method including treating a mixture containing cellulose, a polysaccharide and an aqueous medium together in a wet process, wherein a solid content is controlled to be 35 mass % or more, and temperature is set at 80° C. or less.

5 Claims, 3 Drawing Sheets

(56) References Cited

FOREIGN PATENT DOCUMENTS

| JP | 2008-048604 | 3/2008 | | |
|---|---|---|---|---|
| JP | 2009-291081 | 12/2009 | | |
| JP | 2010-150388 | 7/2010 | | |
| WO | 03/096976 | 11/2003 | | |
| WO | 2003/096976 | 11/2003 | | |
| WO | WO-03096976 A2 * | 11/2003 | ............ | A23C 9/137 |
| WO | 2007/041395 | 4/2007 | | |

OTHER PUBLICATIONS

Partial Supplementary European Search Report issued with respect to Application No. 12822178.5, dated Mar. 18, 2015.
European search report issued for Application No. 12822178.5, dated Jul. 21, 2015.

* cited by examiner

RETENTION TIME (MINUTE)

RETENTION TIME (MINUTE)

HIGHLY FUNCTIONAL CELLULOSE COMPOSITE

CROSS-REFERENCE TO RELATED APPLICATIONS

This is a Divisional application of U.S. application Ser. No. 14/237,688, filed Feb. 7, 2014, which is a National Stage of the International Application No. PCT/JP2012/070495, which claims priority to Japanese Application No. 2011-176177, filed Aug. 11, 2011. The disclosure of application Ser. No. 14/237,688 and PCT/JP2012/070495 are expressly incorporated by reference herein in their entireties.

TECHNICAL FIELD

The present invention relates to a highly functional cellulose composite providing a stable suspension state at a low viscosity for a long time even if it is added in a small amount to foods and drinks such as cocoas, coffees, teas and milks; industrial products such as abrasives and paints; and medicinal products such as syrups. The present invention also relates to beverages such as cereal milk beverages, in which a water-insoluble substance is blended in a high concentration, having excellent suspension stability, texture and taste and flavor due to addition of the cellulose composite.

BACKGROUND ART

A cellulose composite of cellulose and a polysaccharide has been conventionally known to form cellulose colloid in an aqueous medium and show satisfactory suspension stability and is widely used in the fields of e.g., foods, medicinal products, cosmetics, paints, ceramics, resins, catalysts and other industrial products. Particularly, a cellulose composite is used, e.g., as a stabilizer such as a suspension stabilizer, an emulsification stabilizer and a thickening stabilizer, a texture imparting agent, a clouding agent, a whitening improvement, a flowability improvement, a polisher, a dietary fiber and an alternate material for a fat and oil. For example, in a beverage, e.g., calcium enriched milk, a cellulose composite is added for stabilizing suspension of high-gravity water-insoluble components like milk calcium and calcium carbonate.

Recently, in the field of canned or PET bottled tasty beverages such as cocoa, coffee and tea, products containing components such as cocoa, a coffee extract and a tea extract in high concentrations have been developed for providing rich-taste to them. Generally, if the extract as mentioned above is added in a high concentration, the resultant beverage becomes unstable and a water-insoluble component such as a protein is likely to precipitate. Thus, development of a cellulose composite with higher suspension stability compared to conventional composites has been desired.

Here, to improve the suspension-stability effect of a cellulose composite, various studies have been made.

Patent Literature 1 discloses a water-dispersible composite containing micro cellulose and carboxymethylcellulose sodium.

Patent Literature 2 discloses a water dispersible composition containing micro cellulose and a carboxymethylcellulose sodium of specific physical properties such as viscosity and substitution degree and a food composition containing the water dispersible composition. The water dispersible composition is described to show excellent suspension stability and emulsion stability under an acidic environment.

Patent Literature 3 discloses a stabilizer containing water dispersible cellulose, which contains fine fibrous cellulose that is stably suspended in water and a polysaccharide. The stabilizer serves for fixing particles in an acidic or high salt concentration food and drink such as yogurt, fruit sauce and dressing, contributing to providing commercial products having good appearance. Moreover, Patent Literature 4 describes a fermented cellulose composite. Since the fermented cellulose composite is excellent in dispersion stability and suspension stability, it is used in various types of milk-containing beverages and stable acidic milk beverages can be produced.

Patent Literature 5 discloses a method of obtaining a cellulose composite from crystalline cellulose and sodium carboxymethylcellulose as raw materials by grinding them in a solid content of 35 to 60 mass %, as a method of producing a dispersion stabilizer for solid particles.

CITATION LIST

Patent Literature

Patent Literature 1: JP 40-12174 B
Patent Literature 2: JP 9-3243 A
Patent Literature 3: JP 2008-48604 A
Patent Literature 4: JP 2009-291081 A
Patent Literature 5: GB 1190112

SUMMARY OF INVENTION

Technical Problem

However, conventional cellulose composites constituted of cellulose and a polysaccharide are likely to cause aggregation and separation particularly in rich-taste beverages containing a component such as cocoa, a coffee extract and a tea extract in a high concentration and the function as a stabilizer was not sufficiently achieved.

In the cellulose composites or water dispersible compositions described in Patent Literatures 1 and 2, microcellulose itself has satisfactory dispersion stability. However, in rich-taste beverages containing a component in a high concentration, suspension stability thereof was insufficient. In addition to this problem, also in the case where a water-insoluble component such as a functional food material is added, suspension stability is insufficient and problems of sedimentation and aggregation occurred.

The fine fibrous cellulose or fermented cellulose described in Patent Literatures 3 and 4 has an extremely thin and long shape and thus the storage elastic modulus (G') of a water dispersion becomes excessively high. As a result, it caused a problem: the texture (feeling in the throat) of a food and drink containing the fermented cellulose becomes heavy. In addition, if the additive amount of the fermented cellulose is reduced to control texture, a problem of aggregation with a component of a food and drink has occurred.

Patent Literature 5 does not describe temperature control in a step of grinding at all. Furthermore, the carboxymethylcellulose to be used herein has an extremely high viscosity (2200 cps, 1 mass %) and the carboxymethylcellulose is used alone. And the invention of Patent Literature 5 differs from the present invention in which temperature range, and the amount of consumed power are accurately controlled in a grinding step. Accordingly, the cellulose composite (Comparative Example 1 of the present application) obtained by the method of the Patent literature 5 has a small median size measured by a dynamic light scattering method and a small storage elastic modulus. As a result, when beverages were prepared by using the composite of the Patent literature 5, beverages having satisfactory suspension stability, texture and taste and flavor were not obtained.

An object of the present invention is to provide a cellulose composite having low viscosity and excellent dispersion stability and suspension stability for a long time. Another object is to provide a cellulose composite having excellent suspension stability that has never ever been attained in the prior art in food and drink containing a water-insoluble component such as a functional food material.

Hereinbelow, the "dispersion stability" and "suspension stability" used in the specification of the present application is defined.

The "dispersion stability" refers to the dispersion stability of a cellulose composite itself when the cellulose composite is dispersed in an aqueous medium. More specifically, the "dispersion stability" means that the aqueous medium gives homogenous appearance without causing e.g., separation, aggregation or sedimentation of cellulose particles.

The "suspension stability" means that when an aqueous medium contains the components other than a cellulose composite, such as cocoa powder, calcium and a functional food material, these components are effectively suspended and stabilized by the addition of the cellulose composite. More specifically, the "suspension stability" means that the aqueous medium gives homogenous appearance without causing e.g., separation, aggregation or sedimentation of not only cellulose but also other component particles.

Solution to Problem

The present inventors produced a composite of cellulose and a polysaccharide so as to have a high composite degree. They found that if the cellulose composite, which contains a colloidal cellulose composite with a predetermined median size in a predetermined amount is added to a rich-taste beverage containing a component such as coffee, cocoa and a tea extract in a high concentration, in a small amount, the resultant beverage becomes low in viscosity and excellent in suspension stability. Based on the finding, they accomplished the present invention.

More specifically, the present inventors found that, in kneading cellulose and a polysaccharide, if a semisolid-state kneading mixture having a high viscosity due to the presence of a solid substance in a predetermined concentration or more, is kneaded under application of high kneading energy, the kneading energy easily transmits to the kneading mixture. As a result, they found that formation of a composite of cellulose and a polysaccharide is facilitated and spread of a polysaccharide from cellulose in the colloidal cellulose composite contained in the cellulose composite increases, in other words, the median size measured by a dynamic light scattering method increases, and that the resultant cellulose composite exhibits low viscosity and high suspension stability for a long time.

To describe more specifically, the present invention is as follows:

(1) A cellulose composite containing cellulose and a polysaccharide, wherein a median size of colloidal cellulose composites contained in the cellulose composite as measured by a dynamic light scattering method is 0.85 μm or more.
(2) The cellulose composite according to (1), wherein the cellulose composite has a storage elastic modulus (G') of 0.50 Pa or more in a water dispersion of pH 6 to 7 which contains the cellulose composite in an amount of 1 mass %.
(3) The cellulose composite according to (1) or (2), wherein the cellulose composite contains a colloidal cellulose composite in an amount of 50 mass % or more.
(4) The cellulose composite according to any one of (1) to (3), wherein the cellulose composite contains cellulose of 50 to 99 mass % and a polysaccharide of 1 to 50 mass %.
(5) The cellulose composite according to any one of (1) to (4), wherein the polysaccharide is an anionic polysaccharide.
(6) The cellulose composite according to (5), wherein the anionic polysaccharide is sodium carboxymethylcellulose.
(7) The cellulose composite according to any one of (1) to (6), wherein the anionic polysaccharide contains xanthan gum in addition to sodium carboxymethylcellulose.
(8) A food and drink comprising the cellulose composite according to any one of (1) to (7).
(9) A medicinal product comprising the cellulose composite according to any one of (1) to (7).
(10) An industrial product comprising the cellulose composite according to any one of (1) to (7).
(11) A food and drink, a medicinal product or an industrial product comprising the cellulose composite according to any one of (1) to (7) and a water-insoluble component in an aqueous medium and having loss tangent tan δ (loss elastic modulus G"/storage elastic modulus G') of 1.5 or more.
(12) The food and drink according to (11), wherein the water-insoluble component is cocoa powder, cereal powder, fruit, or calcium, magnesium, zinc or a salt thereof.
(13) The food and drink according to (11) or (12), wherein the food and drink is an aqueous beverage, a milk beverage or a fruit beverage.
(14) A method for producing the cellulose composite according to any one of (1) to (7), comprising a step of treating a mixture containing cellulose, a polysaccharide and an aqueous medium together in a wet process, wherein a solid content is controlled to be 35 mass % or more, and temperature is set at 80° C. or less.
(15) The method for producing the cellulose composite according to (14), wherein the polysaccharide is sodium carboxymethylcellulose and the sodium carboxymethylcellulose has a molecular-weight distribution, which is obtained by gel permeation chromatography performed in a 0.05 M sodium hydroxide, having two (bimodal) peaks or more.
(16) The method for producing the cellulose composite according to (14) or (15), wherein the sodium carboxymethylcellulose contains Component A having a viscosity of 100 mPa·s or more and Component B having a viscosity of less than 100 mPa·s in a mass ratio of 5/95 to 95/5.
(17) The method for producing the cellulose composite according to (15) or (16), wherein the sodium carboxymethylcellulose has a substitution degree of 1 or more.
(18) A food and drink, a medicinal product, an industrial product containing a cellulose composite and a water-insoluble component in an aqueous medium and having a loss tangent, tan δ (loss elastic modulus G"/storage elastic modulus G') of 1.5 or more.
(19) A method for producing a cellulose composite, comprising a step of treating a mixture containing a cellulose, a polysaccharide and an aqueous medium together in a wet process, wherein a solid content is controlled to be 35 mass % or more and temperature is set at 80° C. or less.
(20) The method for producing the cellulose composite according to (19), wherein the polysaccharide is sodium carboxymethylcellulose and the sodium carboxymethylcellulose has a molecular-weight distribution, which is obtained by gel permeation chromatography performed in a 0.05 M sodium hydroxide, having two (bimodal) peaks or more.

Advantageous Effects of Invention

The present invention can provide a cellulose composite having low viscosity and excellent suspension stability. Owing to the addition of the cellulose composite of the present invention to a rich-taste beverage containing a component such as coffee, cocoa and a tea extract in a high concentration, foods and drinks having low viscosity and excellent suspension stability for a long time can be provided. Furthermore, when a water-insoluble component such as a functional food material is added to these foods and drinks, foods and drinks giving homogeneous appearance and having excellent suspension stability can be provided while suppressing e.g., separation, aggregation or sedimentation thereof.

DESCRIPTION OF EMBODIMENTS

Figure 1:
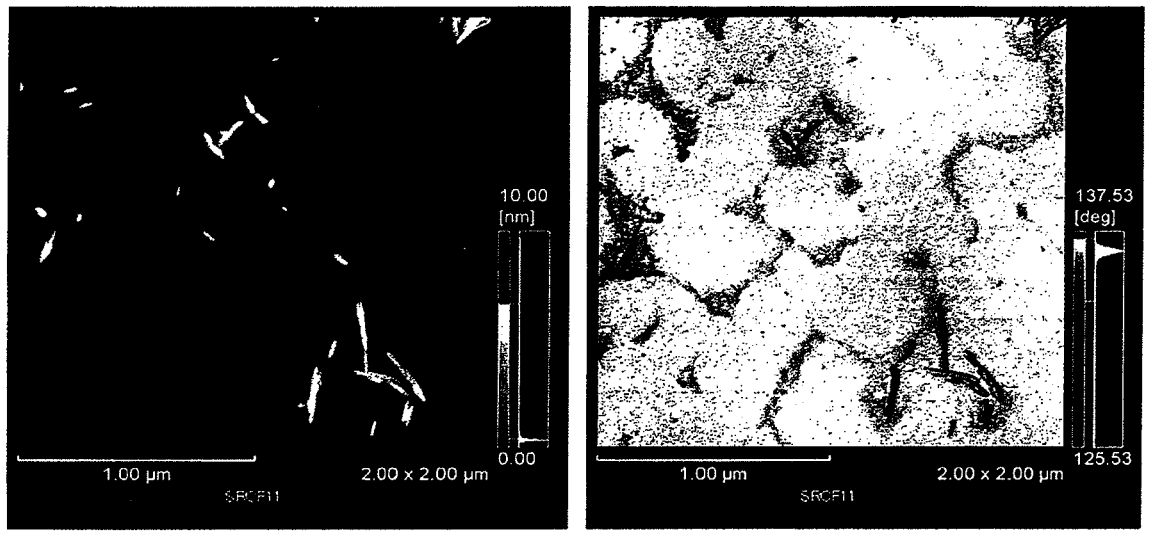
FIG. 1 shows AFM images (the left figure shows an image showing height of a particle and the right figure shows an image formed by phase difference) of cellulose composite D of Example 4.
Figure 2:
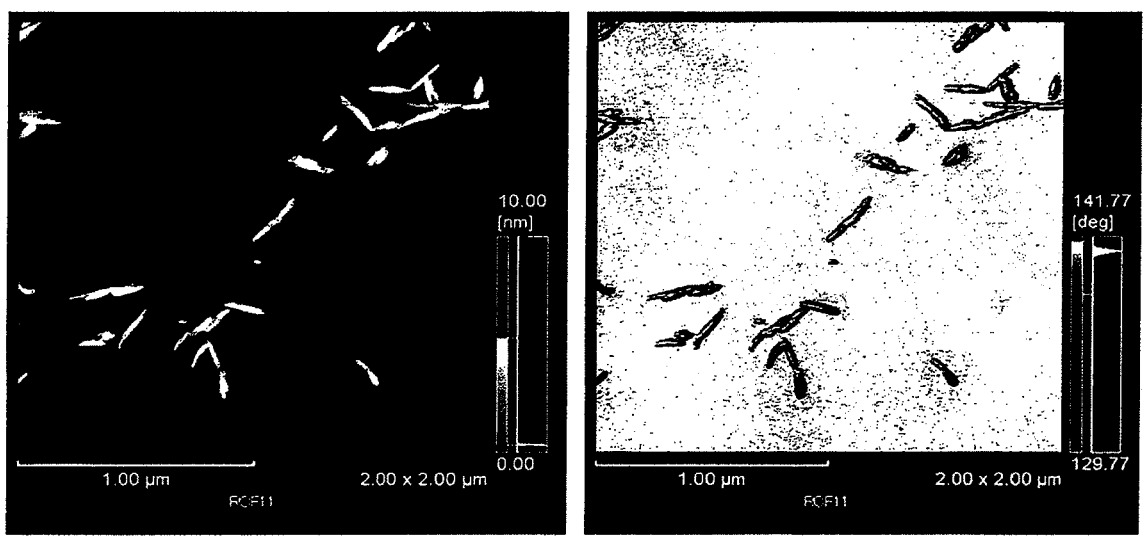
FIG. 2 shows AFM images (the left figure shows an image showing height of a particle and the right figure shows an image formed by phase difference) of cellulose composite G of Comparative Example 1.

The present invention is more specifically described below.

The cellulose composite of the present invention refers to a cellulose composite containing cellulose and a polysaccharide, in which a colloidal cellulose composite contained in the cellulose composite has a median size (measured by a dynamic light scattering method) of 0.85 µm or more. Also, the cellulose composite of the present invention refers to a cellulose composite having a storage elastic modulus (G') of 0.50 Pa or more in a water dispersion of pH 6 to 7 which contains the cellulose composite in an amount of 1 mass %. The formation of a composite used in the present invention means that the surface of cellulose is coated with a polysaccharide with the help of a chemical bond such as a hydrogen bond.

<Cellulose>

In the present invention, the term "cellulose" refers to a naturally derived water-insoluble fibrous substance containing cellulose. Examples of a raw material thereof include wood, bamboo, straw, rice straw, cotton, ramie, bagasse, kenaf, beet, sea squirt and bacteria cellulose. These naturally occurring cellulose materials can be used singly or as a mixture of two types or more, as a raw material.

<Average Polymerization Degree of Cellulose>

As the cellulose to be used in the present invention, crystalline cellulose having an average polymerization degree of 500 or less is preferable. The average polymerization degree can be determined based on the reduced specific viscosity method using a copper ethylene diamine solution, which is defined in the crystalline cellulose identification test (3) of "the 14th edition of the Japanese Pharmacopoeia" (issued by Hirokawa Shoten K.K.). The average polymerization degree is preferably 500 or less because, in the step of forming a composite with a polysaccharide, a cellulose-based substance becomes subject to physical treatment such as stirring, pulverizing and grinding and formation of a composite is easily accelerated. The average polymerization degree is more preferably 300 or less and further preferably 250 or less. The smaller the average polymerization degree, the easier the control of composite formation. Therefore, the lower limit is not particularly limited; however, a preferable range is 10 or more.

<Hydrolysis of Cellulose>

As a method for controlling the average polymerization degree, e.g., a hydrolysis treatment is mentioned. Since depolymerization of amorphous cellulose within a cellulose fiber is accelerated by the hydrolysis treatment, the average polymerization degree decreases. At the same time, since not only the amorphous cellulose mentioned above but also impurities such as hemicellulose and lignin are removed by the hydrolysis treatment, the interior of the fiber becomes porous. By virtue of this, in a step of applying mechanical shearing force to cellulose and a polysaccharide, e.g., in a kneading step, the cellulose becomes subject to mechanical treatment, thus it becomes subject to pulverizing. As a result, the surface area of cellulose increases which allows formation of a composite with a polysaccharide to be easily controlled.

Examples of the hydrolysis method include, but not particularly limited to, acid hydrolysis, hydrothermal degradation, steam explosion and microwave decomposition. These methods may be used singly or in combination of two types or more. In the acid hydrolysis method, the average polymerization degree can be easily controlled by adding, e.g., protonic acid, carboxylic acid, Lewis acid or heteropolyacid to a cellulose substance dispersed in an aqueous medium, in an appropriate amount, and increasing temperature while stirring the obtained mixture. At this time, the reaction conditions such as temperature, pressure and time vary depending upon the type of cellulose, cellulose concentration, type of acid and acid concentration but are appropriately controlled so as to attain a desired average polymerization degree. For example, conditions for treating cellulose by using an aqueous mineral acid solution of 2 mass % or less at 100° C. or more under pressure for 10 minutes or more are mentioned. In these conditions, a catalyst component such as an acid permeates the interior of a cellulose fiber and accelerates hydrolysis, with the result that the use amount of catalyst component decreases and the following purification is easily carried out.

<Shape of Cellulose Particle (L/D)>

The cellulose contained in the cellulose composite of the present invention preferably has a micro particle shape. The particle shape of the cellulose is obtained by preparing a 1 mass % pure water suspension of the cellulose composite of the present invention, dispersing the suspension by a high-shear homogenizer (trade name "Excel autohomogenizer ED-7" manufactured by Nippon Seiki Co., Ltd., treatment conditions: rotation number 15,000 rpm×5 minutes), diluting the resultant water dispersion with pure water to 0.1 to 0.5 mass %, casting the diluted water dispersion onto mica, drying the resultant particles in the air, and measuring thus dried resultant particles under a high-resolution scanning microscope (SEM) or an atomic force microscope (AFM) to obtain the particle images having the major axis (L) and the minor axis (D). The particle shape of the cellulose is represented by a ratio L/D, which is calculated as an average (ratio) value of L/D of 100 to 150 particles.

In view of suspension stability, the L/D value is preferably less than 20, more preferably 15 or less, further preferably 10 or less, particularly preferably 5 or less, especially preferably less than 5 and most preferably 4 or less.

<Polysaccharide>

The polysaccharide in the present invention refers to a compound in which saccharide units such as glucose, galactose, mannose, xylose, N-acetylglucosamine, gluconic acid, galacturonic acid and mannuronic acid are connected via a α or β bond to constitute a main chain or a side chain. Examples of the naturally-derived polysaccharides include resin derived polysaccharides such as almond gum, gum Arabic, arabinogalactan, elemi resin, gum karaya, gum ghatti, dammar resin, gum tragacanth and peach gum; bean-derived polysaccharides such as linseed gum, *cassia* gum, locust bean gum, guar gum, an enzymatic decomposition product of guar gum, *psyllium* seed gum, *Artemisia sphaerocephala* seed gum, *Sesbania* seed gum, *Tamarindus* seed gum, tara gum and *Triacanthos* gum; seaweed-derived polysaccharides such as alginic acid, carrageenan, a Fukuronori extract and furcellaran; polysaccharides derived from fruits, leaves and underground stems such as an aloe vera extract, an okra extract, a krantz aloe extract, Tororoaoi and pectin; and polysaccharides derived from microbial fermentation products such as *Aeromonas* gum, an *Aureobasidium* cultured solution, *Azotobacter vinelandii* gum, welan Gum, *erwinia mitsuensis* gum, *Enterobacter simanus* gum, *Enterobacter* gum, curdlan, xanthan gum, gellan gum, sklero gum, dextran, *Bacillus natto* gum, pullulan, *Macrophomopsis* gum, ramzan gum and levan. Examples of cellulose derived polysaccharides include cellulose, microfibrous cellulose, fermented cellulose, and cellulose derivatives such as methylcellulose, ethylcellulose, hydroxyethylcellulose, hydroxypropylmethylcellulose, hydroxypropylcellulose, carboxymethylcellulose, carboxyethylcellulose and sodium salts and calcium salts thereof. Examples of other polysaccharides include yeast cellwall, chitin, chitosan, glucosamine, oligoglucosamine, heparin and chondroitin sulfate.

These polysaccharides may be used alone or in combination of two or more.

Of them, anionic or neutral polysaccharides are preferable for use in the cellulose composite of the present invention since they are easily formed into a composite with crystalline cellulose. An anionic polysaccharide is further preferable since it is more easily formed into a composite.

<Anionic Polysaccharide>

The polysaccharides, which release cations in water and serve as anions per se are called anionic polysaccharide. An anionic polysaccharide is preferably used in the present invention. This is because formation of a composite with cellulose is further facilitated by using the anionic polysaccharide.

As the anionic polysaccharide, the followings are preferable.

Examples thereof include *psyllium* seed gum, karaya gum, carrageenan, agar, furcellaran, heparin, chondroitin sulfate, alginic acid, sodium alginate, calcium alginate, HM pectin, LM pectin, *Azotobacter vinelandii* gum, xanthan gum, gellan gum and a cellulose derivative such as carboxymethylcellulose sodium, carboxymethylcellulose calcium, sodium carboxyethylcellulose and calcium carboxyethylcellulose. These anionic polysaccharides may be used in combination with two or more types.

<Content of Colloidal Cellulose Composite in Cellulose Composite>

It is preferable that the cellulose composite of the present invention contains a colloidal cellulose composite in an amount of 50 mass % or more. The content of the colloidal cellulose composite herein refers to the mass percentage of a solid content (including cellulose and a polysaccharide, and if the cellulose composite of the present invention contains a water-soluble gum, the water-soluble gum is further included) remaining in the final supernatant, which is obtained by suspending the cellulose composite in pure water in a concentration of 0.5 mass %, dispersing the suspension by a high-shear homogenizer (trade name "Excel auto homogenizer ED-7", manufactured by Nippon Seiki Co., Ltd., treatment conditions: rotation number of 15,000 rpm×5 minutes), centrifuging it by a centrifuge (trade name "6800 type centrifuge" rotor-type RA-400, manufactured by KUBOTA Corporation, treatment conditions: centrifugal force: 39200 m$^2$/s) for 10 minutes, collecting the supernatant and further centrifugally treating the supernatant at a rate of 116000 m$^2$/s for 45 minutes. If the content of a colloidal cellulose composite is 50 mass % or more, the suspension stability improves. The content is further preferably 60 mass % or more and more preferable 70 mass % or more. The higher the content of the colloidal cellulose composite, the higher the suspension stability. Thus, the upper limit of the content, which is not particularly limited, is preferably 100 mass % or less.

<Spread of Polysaccharide of Composite*Median Size Measured by Dynamic Light Scattering Method>

The cellulose composite of the present invention is characterized in that spread of a polysaccharide radially extending from the surface of a cellulose particle is larger than those of conventional composites. The spread of a polysaccharide is represented by the median size of the colloidal cellulose composites measured by a dynamic light scattering method. In the cellulose composite of the present invention, the median size must be 0.85 μm or more.

The median size can be measured by a dynamic light scattering method in the following manner. First, a cellulose composite is suspended in pure water in a concentration of 0.5 mass % and dispersed by a high-shear homogenizer (trade name "Excel auto homogenizer ED-7", manufactured by Nippon Seiki Co., Ltd., treatment conditions: rotation number of 15,000 rpm×5 minutes) and centrifugally separated by a centrifuge (trade name "6800 type centrifuge" rotor-type RA-400, manufactured by KUBOTA Corporation, treatment conditions: centrifugal force of 39200 m$^2$/s) for 10 minutes. Then, the supernatant is collected and further centrifugally treated at 116000 m$^2$/s for 45 minutes. The resultant supernatant was collected, placed in a 50-mL (volume) sample tube made of PP and ultrasonically treated by an ultrasonic cleaner (an ultrasonic cleaner, trade name: AUC-1L type manufactured by AS ONE Corporation) for 10 minutes. Thereafter, a particle size distribution (frequency distribution of scattering intensity versus particle size value) is measured by a zeta potential-particle size measurement system (trade name "ELSZ-2" (batch cell), manufactured by Otsuka Electronic Co., Ltd.). The median size herein refers to a particle size value (μm) corresponding to a cumulative 50% scattering intensity in the frequency distribution. The larger the median size, the more excellent the suspension stability of a cellulose composite. Thus, the median size is preferably 0.90 μm or more, more preferably 1.0 μm or more, further preferably 1.1 μM or more and particularly preferably 1.2 μm or more. The upper limit, which is not particularly limited, is preferably 5.0 μm or less, more preferably 3.0 μm or less, further preferably 2.0 μm or less and particularly preferably 1.5 μm or less.

<Sodium Carboxymethylcellulose>

Of the anionic polysaccharides mentioned above, sodium carboxymethylcellulose (hereinafter referred to as CMC-Na) is particularly preferable since it can easily form a composite with cellulose. The CMC-Na herein refers to a chemical compound obtained by substituting a hydroxy group of cellulose with monochloroacetic acid and having a linear chemical structure of D-glucose units linked via a β-1,4 bond. CMC-Na is obtained by dissolving pulp (cellulose) in a sodium hydroxide solution and substituting with monochloroacetic acid (or a sodium salt thereof).

Particularly, CMC-Na, which is prepared such that its substitution degree and viscosity fall within predetermined ranges, is preferably used in view of formation of a composite.

As the viscosity of CMC-Na, 500 mPa·s or less, which is a viscosity of 1 mass % pure aqueous solution of CMC-Na, is preferable. The viscosity herein is measured in the following manner. First, CMC-Na powder is dispersed in pure water so as to obtain a concentration of 1 mass % by use of a high-shear homogenizer (trade name "Excel auto homogenizer ED-7", manufactured by Nippon Seiki Co., Ltd., treatment conditions: rotation number of 15,000 rpm×5 minutes) to prepare an aqueous solution. Three hours (stored at 25° C.) after the dispersion, the resultant aqueous solution is set in a B-type viscometer (rotor revolving speed: 60 rpm), allowed to stand still for 60 seconds and rotated for 30 seconds, and then, the viscosity is measured. Note that the rotor can be appropriately changed depending upon the viscosity. The lower the viscosity of CMC-Na, the more easily a composite with cellulose and a polysaccharide is formed. Because of this, the viscosity is more preferably 200 mPa·s or less and further preferably 100 mPa·s or less. The lower limit, which is not particularly specified, is preferably 1 mPa·s or more.

<Combination of "CMC-Na">

As the CMC-Na to be used in the cellulose composite of the present invention, preferably two types of CMC-Na different in viscosity are used in combination. Specifically, the combination of CMC-Na preferably contains component A having a viscosity (measured in a 2 mass % aqueous solution thereof at 25° C.) of 100 mPa·s or more and component B having a viscosity (measured in a 2 mass % aqueous solution thereof at 25° C.) of less than 100 mPa·s in a blending ratio, i.e. Component A/Component B=5/95 to 95/5 (mass ratio).

The viscosity herein is measured in the following manner. First, CMC-Na powder is dispersed in a pure water so as to obtain a concentration of 2 mass % by use of a high-shear homogenizer (trade name "Excel auto homogenizer ED-7", manufactured by Nippon Seiki Co., Ltd., treatment conditions: rotation number of 15,000 rpm×5 minutes) to prepare an aqueous solution. Then, three hours (stored at 25° C.) after the dispersion, the resultant aqueous solution is set in B-type viscometer (rotor revolving speed: 60 rpm), allowed to stand still for 60 seconds and rotated for 30 seconds. In this manner, the viscosity is measured. Note that the rotor can be appropriately changed depending upon the viscosity.

Herein, Component A (high-viscosity CMC-Na), when it is combined with cellulose into a composite, radially spreads from the surface of the cellulose if the composite is dispersed in water and tangled with CMC-Na of the adjacent composite. In this manner, a rigid network structure of the cellulose composites is made, with the result that the storage elastic modulus (G') of a water dispersion increases. The viscosity of Component A is preferably set within a proper range. This is because the spread of CMC-Na from the cellulose surface increases. The viscosity of Component A is more preferably 200 mPa·s or more, further preferably 300 mPa·s or more and particularly preferably 500 mPa·s or more. The upper limit is preferably 10000 mPa·s or less, more preferably 5000 mPa·s or less, further preferably 2000 mPa·s or less and particularly preferably 1000 mPa·s or less.

Component B (low-viscosity CMC-Na) serves to stiffen the mixture of cellulose and a polysaccharide to be kneaded. As a result, power can be easily applied to the kneading mixture, facilitating formation of a composite effectively in a predetermined time. The viscosity of Component B is correlated with the above-mentioned composite-formation facilitating effect. The viscosity of Component B is more preferably 90 mPa·s or less, further preferably 70 mPa·s or less, particularly preferably 50 mPa·s or less and most preferably 30 mPa·s or less. The lower limit is preferably 1 mPa·s or more, more preferably 5 mPa·s or more, further preferably 10 mPa·s or more and particularly preferably 20 mPa·s or more.

Depending upon the blending ratio of Component A and Component B, easiness in forming a cellulose composite and function of the resultant cellulose composite can be adjusted. As the blending ratio (mass ratio), Component A/Component B=10/90 to 90/10 is more preferable, 20/80 to 80/20 is further preferable, 30/70 to 70/30 is particularly preferable and 40/60 to 60/40 is most preferable.

<Molecular-Weight Distribution of CMC-Na>

The CMC-Na to be used in the present invention preferably has a chromatogram having two (bimodal) peaks or more, which is obtained in measuring the molecular weight of CMC-Na by gel permeation chromatography (GPC).

Two (bimodal) peaks or more means that a GPC chromatogram has a curve having two or more discrete peaks (two peak tops or more). The curve having such a shape means that the molecular-weight distribution is not monodispersed. Since a plurality of components are mixed, the components mutually compensate, with the result that spread of CMC-Na from the surface of cellulose increases to obtain a cellulose composite having high G'.

The gel permeation chromatography herein is performed by use of a high performance liquid chromatographic (HPLC) apparatus (trade name Type LC-20A, manufactured by Shimadzu Corporation), to which a single column (trade name TSK-GEL G5000PW type (7.8 mm×30 cm), manufactured by Tosoh Corporation) and two columns (trade name TSK-GEL G3000 PWXL type (7.8 mm×30 cm)) are connected in line. Measurement is performed by supplying an aqueous 0.05 mol/L sodium hydroxide solution as a mobile phase, at a flow rate of 1 mL/minute and setting a column temperature at 30° C. Detection is made by an RI detector or a UV detector (wavelength: 210 nm) to obtain a chromatogram. In the resultant chromatogram, two (bimodal) peaks or more are detected.

CMC-Na to be used herein is completely dissolved in the same solution as used in the above mobile phase and then put in use. The concentration of the CMC-Na solution is appropriately adjusted within the range of 0.01 to 1.0 mass %. Measurement is performed by injecting the CMC-Na solution in a dose of 5 to 10 μL/time.

Owing to the use of CMC-Na, whose molecular weight distribution is not single dispersion but has at least two (bimodal) peaks, the surface charge of the cellulose composite becomes high and CMC-Na spreads more widely. For this reason, CMC-Na having a molecular weight distribution of two (bimodal) peaks or more is preferably used.

<Substitution Degree of CMC-Na>

CMC-Na to be used in the cellulose composite of the present invention preferably has a high substitution degree. This is because the higher the substitution degree of CMC-Na, the more easily CMC-Na is combined with cellulose into a composite, with the result that the cellulose composite exhibits a higher storage elastic modulus and high suspension stability even in an aqueous solution having a high salt concentration (for example, an aqueous 10 mass % sodium chloride solution). Furthermore, owing to use of CMC-Na having a high substitution degree, excessive aggregation with a protein such as a milk component rarely occurs. The substitution degree refers to a ratio of a carboxymethyl group binding to a hydroxy group of cellulose via an ether bond. Specifically, the substitution degree is preferably 0.5 or more, more preferably 1.0 or more, further preferably 1.2 or more and particularly preferably 1.3 or more. The upper limit is preferably 3 or less, more preferably 2 or less and further preferably 1.5 or less.

The substitution degree herein is measured in the following manner. A sample (anhydride) (0.5 g) is accurately weighed, wrapped with a filter and baked in a magnetic crucible into ash. After cooling, this is transferred to a 500 mL beaker. To the beaker, water (about 250 mL) and 0.05 M sulfuric acid (35 mL) are added. The mixture is boiled for 30 minutes. The resultant mixture is cooled and a phenolphthalein indicator is added. Excessive acid is neutralized by back titration with 0.1 M potassium hydroxide. The substitution degree is calculated by the following expressions.

$$A = ((af - bf1)/\text{sample anhydride (g)}) - \text{alkali level (or +acid level)}$$

$$\text{Substitution degree} = (162 \times A)/(10000 - 80A)$$

where
A: Amount of 0.05 M sulfuric acid (mL) consumed by alkali per sample (1 g)
a: Use amount of 0.05 M sulfuric acid (mL)
f: Titer of 0.05 M sulfuric acid
b: Titer (mL) of 0.1 M potassium hydroxide
f1: Titer of 0.1 M potassium hydroxide
162: Molecular weight of glucose
80: Molecular weight of $CH_2COONa$—H Method of Measuring Alkali Level (or Acid Level):

A sample (anhydride) (1 g) is accurately weighed in a 300 mL-flask. To this flask, water (about 200 mL) is added to dissolve the sample. To this, 0.05 M sulfuric acid (5 mL) is added and the mixture is boiled for 10 minutes and cooled. To this resultant mixture, a phenolphthalein indicator is added and titrated with 0.1 M potassium hydroxide (S mL). At the same time, a blank test is performed (B mL). The alkali level is calculated in accordance with the following expression.

$$\text{Alkali level} = ((B - S) \times f)/\text{sample anhydride (g)}$$

where f: Titer of 0.1 M potassium hydroxide. If a value of {(B−S)×f} is a negative value (−), the alkali level is regarded as an acid level.

<Blending Ratio of Cellulose and Polysaccharide>

The cellulose composite of the present invention preferably contains cellulose in an amount of 50 to 99 mass % and a polysaccharide in an amount of 1 to 50 mass %. In forming a composite, the surface of a cellulose particle is coated with a polysaccharide via a chemical bond such as a hydrogen bond. By virtue of this, when such a cellulose composite is dispersed in a neutral aqueous solution, the suspension stability of the cellulose composite improves. Furthermore, formation of a composition is facilitated by using cellulose and a polysaccharide satisfying the aforementioned contents and the suspension stability of the neutral water dispersion improve to easily attain an effect of preventing sedimentation of a water-insoluble component such as a functional food material. The cellulose composite of the present invention more preferably contains cellulose in an amount of 70 to 99 mass % and a polysaccharide in an amount of 1 to 30 mass %, further preferably contains cellulose in an amount of 80 to 99 mass % and a polysaccharide in an amount of 1 to 20 mass % and particularly preferably contains cellulose in an amount of 85 to 99 mass % and a polysaccharide in an amount of 1 to 15 mass %.

<Particle Size of a Cellulose Core in Cellulose Composite*Median Size by Laser Diffraction/Scattering Method>

The median size of the colloidal cellulose composites in the cellulose composite of the present invention, as measured by a laser diffraction/scattering method, is preferably 1.0 μm or less. The median size measured by this method represents the particle size of a cellulose core present at the center of the cellulose composite, different from that measured by the dynamic light scattering method as mentioned above. The median size can be measured by the laser diffraction/scattering method in the following manner.

First, a cellulose composite is suspended in pure water in a concentration of 0.5 mass %, dispersed by a high-shear homogenizer (trade name "Excel auto homogenizer ED-7", manufactured by Nippon Seiki Co., Ltd., treatment conditions: rotation number of 15,000 rpm×5 minutes), centrifugally separated by a centrifuge (trade name "6800 type centrifuge" rotor-type RA-400, manufactured by KUBOTA Corporation, treatment conditions: centrifugal force of 39200 m²/s) for 10 minutes. The supernatant is collected and further centrifugally treated at a rate of 116000 m²/s for 45 minutes and the resultant supernatant is collected. The supernatant is measured by a laser diffraction/scattering particle size distribution meter (trade name "LA-910" manufactured by Horiba, Ltd. ultrasonic treatment: 1 minute, refractive index 1.20). In the obtained volume frequency particle size distribution, the cumulative 50% particle size (a volume average particle size) is the particle size of a cellulose core in cellulose composite. The smaller the value of this particle size, the more preferable because the suspension stability of a cellulose composite becomes excellent. The value is more preferably 0.7 μm or less, further preferably 0.5 μm or less, particularly preferably 0.3 μm or less and most preferably 0.2 μm or less.

<Size of Coarse Particles in Cellulose Composite*the Median Size by Laser Diffraction/Scattering Method>

The cellulose composite of the present invention is characterized in that the median size of coarse particles contained therein is small. The size of the coarse particles can be measured in the following manner. First, a cellulose composite is suspended in pure water in a concentration of 0.5 mass % and dispersed by a high-shear homogenizer (trade name "Excel auto homogenizer ED-7", manufactured by Nippon Seiki Co., Ltd., treatment conditions: rotation number of 15,000 rpm×5 minutes). The dispersion is directly (without subjecting to centrifugal separation) subjected to a laser diffraction/scattering particle size distribution meter (trade name "LA-910" manufactured by Horiba, Ltd. ultrasonic treatment: 1 minute, refractive index 1.20). In the obtained volume frequency particle size distribution, the cumulative 50% particle size (volume average particle size) is the size of coarse particles in cellulose composite. The median size is preferably 20 μm or less, because the suspension stability of a cellulose composite is more easily improved. Furthermore, if the cellulose composite is contained in food, food having smooth texture without grainy feeling on tongue can be provided. The median size is more preferably 15 μm or less, particularly preferably 10 μm or less, and further preferably 8 μm or less. The lower limit, which is not particularly limited, is preferably 0.1 μM or more.

<Storage Elastic Modulus of Cellulose Composite>

Next, the storage elastic modulus (G') of the cellulose composite of the present invention is described.

The cellulose composite of the present invention has a storage elastic modulus (G') of 0.50 Pa or more, which is obtained as the storage elastic modulus in a water dispersion of pH 6 to 7 containing 1 mass % of the cellulose composite. The storage elastic modulus represents rheological elasticity of a water dispersion, and represents degree of composite formation between cellulose and a polysaccharide or degree of composite formation between cellulose and a polysaccharide and another water soluble gum. A higher storage elastic modulus means that the composite formation between cellulose and a polysaccharide or the composite formation between cellulose and a polysaccharide and another water soluble gum is accelerated to form a rigid network structure of a cellulose composite in a water dispersion. The more rigid the network structure becomes, the more excellent the suspension stability a cellulose composite has.

In the present invention, the storage elastic modulus is defined as a value obtained by measuring dynamic viscoelasticity of a water dispersion (pH 6 to 7) in which a cellulose composite is dispersed in pure water. When distortion is given to the water dispersion, the elastic component which keeps stress stored within a cellulose composite network structure, is expressed as a storage elastic modulus.

A method for measuring storage elastic modulus is as follows: first, a cellulose composite is dispersed in pure water by use of a high-shear homogenizer (trade name "Excel autohomogenizer ED-7" manufactured by Nippon Seiki Co., Ltd., treatment conditions: rotation number 15,000 rpm×5 minutes) to prepare a 1.0 mass % pure water dispersion. The resultant water dispersion is allowed to stand still at room temperature for 3 days. The distortion-dependent stress of the water dispersion is measured by a viscoelasticity measurement apparatus (ARES100FRTN1 type, manufactured by Rheometric Scientific, Inc., geometry: Double Wall Couette type, sweeping is performed at a constant temperature at 25.0° C. and an angular velocity of 20 rad/second within a distortion range of 1 to 794%; a water dispersion is slowly supplied by use of a dropper so as not to destroy a microstructure and allowed to stand still for 5 minutes and then measurement is initiated by Dynamic Strain mode). The storage elastic modulus of the present invention refers to a value corresponding to a distortion of 20% on the distortion-stress curve obtained by the aforementioned measurement. The larger the storage elastic modulus value, the more elastic the structure of the water dispersion formed of the cellulose composite, and this represents that cellulose and a polysaccharide, or cellulose and a polysaccharide and another water soluble gum are highly combined.

The storage elastic modulus of a cellulose composite is preferably 0.75 Pa or more, more preferably 1.0 Pa or more, further preferably 1.3 Pa or more, particularly preferably 1.6 Pa or more and most preferably 1.8 Pa or more.

The upper limit thereof is not particularly determined; however, in view of easy-to-take as a beverage, the upper limit is 6.0 Pa or less. The upper limit of 6.0 Pa or less is preferable because a beverage containing a cellulose composite in the additive amount (which varies depending upon the beverage, for example, 0.1 to 1.0 mass %, in tasty beverages such as coffee, cocoa and tea or beverages such as Ca-enriched milk) at which suspension stability is sufficiently obtained, gives light feeling in the throat. Furthermore, even in the case where the additive amount of cellulose composite is lowered to control texture (for example, 0.5 mass % or less), aggregation or the like with a water insoluble component other than cellulose rarely occurs.

<Structure of Cellulose Composite>

The cellulose composite of the present invention is characterized in the spreading of a polysaccharide radially extending from the surface of cellulose is large, compared to the conventional products. The larger the spreading of a polysaccharide extending from the surface of cellulose, the easier to get tangled with adjacent polysaccharide of the cellulose composite. As a result, cellulose composites get tangled densely with each other to obtain a rigid network structure. In this manner, storage elastic modulus (G') improves, and suspension stability increase. The spreading of a polysaccharide can be measured by the following method.

First, a cellulose composite is dispersed by a high-shear homogenizer (trade name "Excel autohomogenizer ED-7" manufactured by Nippon Seiki Co., Ltd., treatment conditions: rotation number 15,000 rpm×5 minutes, total amount 300 g) in pure water to prepare a 1.0 mass % pure water dispersion. The resultant water dispersion is allowed to stand still at room temperature for 3 days or more. Thereafter, the water dispersion is diluted 20 folds with pure water to prepare a sample solution. From the water dispersion, an aliquot (5 μl) is slowly suctioned by use of a dropper so as not to destroy a microstructure of the water dispersion and allowed to slowly fall in drops on cleaved mica (1 cm×1 cm). After extra moisture content is blown out by an air duster, the sample deposited on the mica is observed by AFM (scanning probe microscope SPM-9700, manufactured by Shimadzu Corporation, phase mode, as a probe, OMCL-AC240TS manufactured by Olympus Corporation is used). In the image under observation, a cellulose particle is seen as a rod-form particle having a height of 2 nm or more and a polysaccharide having a height of less than 2 nm radially extended from the cellulose particle peripherally can be observed (FIG. 1). In the present invention, spread of a polysaccharide radially extending from a cellulose particle is expressed by the median size of the colloidal cellulose composites measured by a dynamic light scattering method.

A polysaccharide preferably has a high composite degree, because the spread of the polysaccharide becomes larger. Furthermore, if CMC-Na having a predetermined substitution degree and viscosity is used as a polysaccharide, the spread becomes larger. If two types of CMC-Na having predetermined viscosity values are used in combination, the spread becomes further larger.

<Viscosity of Water Dispersion of Cellulose Composite>

The cellulose composite of the present invention is characterized in that since spread of CMC-Na from a cellulose particle is large as mentioned above, the cellulose particle easily gets tangled with the adjacent particle in a water dispersion. Because of this, the cellulose composite of the present invention has higher viscosity than conventional products. In addition, if the cellulose composite is added to a food and drink, it can provide satisfactory textures such as rich-taste and smooth sensation going down the throat (easy-to-take). The viscosity herein can be measured in the following manner.

First, a cellulose composite is dispersed in pure water by use of a high-shear homogenizer (trade name "Excel auto homogenizer ED-7", manufactured by Nippon Seiki Co., Ltd., treatment conditions: rotation number of 15,000 rpm×5 minutes) to prepare a dispersion in pure water having a concentration of 1.0 mass %. Three hours (stored at 25° C.) after the dispersion, the water dispersion is set in B-type viscometer (rotor revolving speed: 60 rpm), allowed to stand still for 30 seconds and rotated for 30 seconds, and then, the viscosity is measured. Note that the rotor can be appropriately changed depending upon the viscosity. The rotors used herein are as follows: 1 to 20 mPa·s: BL type, 21 to 100 mPa·s: No. 1, 101 to 300 mPa·s: No. 2, 301 mPa·s or more: No. 3.

A preferable range of viscosity of a water dispersion of cellulose composite is 100 mPa·s or more. The range is more preferably 150 mPa·s or more, further preferably 200 mPa·s or more, further more preferably 250 mPa·s or more, particularly preferably 300 mPa·s or more, and most preferably 350 mPa·s or more. The upper limit, which is closely connected to easy-to-take, is preferably 1000 mPa·s or less, more preferably 700 mPa·s or less, further preferably 600 mPa·s or less and particularly preferably 500 mPa·s or less.

<Water Soluble Gum>

It is preferable that the cellulose composite of the present invention further contains a water soluble gum other than a polysaccharide. As the water soluble gum, a gum highly swellable and easily forming a composite with cellulose is preferable.

Examples thereof include locust bean gum, guar gum, tamarind seed gum, karaya gum, chitosan, gum arabic, agar, carrageenan, alginic acid, alginate such as sodium alginate, calcium alginate, pectins such as HM pectin, LM pectin, *Azotobacter vinelandii* gum, xanthan gum, curdlan, pullulan, dextran, gellan gum, gelatin, cellulose derivatives such as carboxymethylcellulose calcium, methylcellulose, hydroxypropylcellulose and hydroxyethylcellulose. They may be used in combination of two types or more.

Among the water-soluble gums mentioned above, in view of formation of a composite with cellulose, xanthan gum, karaya gum, gellan gum, pectin and alginate are preferable.

<Mass Ratio of Polysaccharide and Water Soluble Gum>

The mass ratio of a polysaccharide and a water soluble gum as mentioned above is preferably 30/70 to 99/1. In the cellulose composite of the present invention, if the ratio of a polysaccharide and a water soluble gum as mentioned above falls within the above range, the cellulose composite of the present invention exhibits suspension stability in a water dispersion containing the cellulose composite of the present invention within a broad pH range from weak alkaline (pH8) to acidic (pH3). The content ratio of a polysaccharide and a water soluble gum is more preferably 40/60 to 90/10 and further preferably 40/60 to 80/20.

<Hydrophilic Substance>

To improve dispersibility to water, a hydrophilic substance other than a polysaccharide and a water soluble gum may be further added to the cellulose composite of the present invention. The hydrophilic substance refers to an organic substance highly soluble in cool water and rarely increasing viscosity. Examples of suitable organic substance include hydrophilic polysaccharides such as a starch hydrolysate, dextrins, an indigestible dextrin, and a polydextrose; oligosaccharides such as fructo-oligosaccharide, galactooligosaccharide, maltooligosaccharide, isomaltooligosaccharide, lactose, maltose, sucrose and α-, β- and γ-cyclodextrin; monosaccharides such as glucose, fructose and sorbose; and sugar alcohols such as maltitol, sorbitol and erythritol. These hydrophilic substances may be used in combination with two types or more. Of the aforementioned organic substances, a hydrophilic polysaccharide, such as a starch hydrolysate, dextrins, an indigestible dextrin and a polydextrose, is preferable in view of dispersibility.

Other components may be freely added to the extent that they do not disturb dispersibility and stability of a composition in water.

<Method for Producing Cellulose Composite>

Next, a method for producing the cellulose composite of the present invention is described.

The cellulose composite of the present invention containing a colloidal cellulose composite having a predetermined median size in a predetermined amount is obtained by applying mechanical shearing force to cellulose and a polysaccharide in a kneading step to make cellulose into small pieces, and combining the polysaccharide to the surface of the cellulose pieces to make a composite. Furthermore, a water soluble gum other than a polysaccharide, hydrophilic substance and other additives may be added. The composite obtained through the treatment in the aforementioned process is, if necessary, dried. The cellulose composite of the present invention subjected to the aforementioned mechanical shearing may be in any state such as undried and dried.

To apply mechanical shearing force, a kneading method using a kneading machine, etc. can be used. Examples of the kneading machine include a kneader, an extruder, a planetary mixer and a grinder (Raikai mixer). They may be used in a continuous system or a butch system. As the kneading temperature, a natural process temperature may be used; however, if heat is generated from a reaction for forming a composite and friction, etc. during a kneading process, kneading may be performed while removing the generated heat. These machines may be used singly or in combination of two types or more. These machines may be appropriately selected depending upon the requirement of viscosity, etc., in various uses.

Furthermore, the lower the kneading temperature, the more suppressed the deterioration of a polysaccharide, with the result that the storage elastic modulus of a cellulose composite (G') increases and thus preferable. The kneading temperature is preferably 80° C. or less, more preferably 70° C. or less, further preferably 60° C. or less, more further preferably 50° C. or less, particularly preferably 30° C. or less and most preferably 20° C. or less. To maintain the above-mentioned kneading temperature under high energy, it is free to use a cooling means such as jacket cooling and heat radiation.

The solid content during a kneading process is preferably 35 mass % or more. If the mixture in a semisolid state having high viscosity is kneaded, the kneaded mixture does not become watery and thus kneading energy as described below can be easily transferred to the kneaded mixture to facilitate formation of a composite and thus preferable. The solid content during a kneading process is more preferably 40 mass % or more, further preferably 50 mass % or more and particularly preferably 55° C. mass % or more. The upper limit is not particularly limited; however, in consideration of avoiding dry state (low-moisture content) of a kneaded mixture and obtaining a sufficient kneading effect and homogeneous kneading state, a practical range is preferably 90 mass % or less, more preferably 70 mass % or less and further preferably 60 mass % or less. Furthermore, to adjust the solid content so as to fall within the above range, a necessary amount of water may be added before a kneading step or during the kneading step or both timings.

Hereinbelow, kneading energy is described. The kneading energy is defined by electric energy per unit mass (Wh/kg) of a kneaded mixture. The kneading energy is preferably 50 Wh/kg or more. If the kneading energy is 50 Wh/kg or more, the grinding power given to the kneaded mixture is high and formation of a composite between cellulose and a polysaccharide or between cellulose, a polysaccharide and another water soluble gum, etc. is accelerated, with the result that, the suspension stability of a neutral cellulose composite is improved. The kneading energy is more preferably 80 Wh/kg or more, further preferably 100 Wh/kg or more and particularly preferably 200 Wh/kg or more, further more preferably 300 Wh/kg or more and most preferably 400 Wh/kg or more.

It is considered that the higher the kneading energy becomes, the more the formation of a composite is facilitated. However, if the kneading energy is excessively high, excessively large equipment is industrially required. Since excessively large load is applied to the equipment, the upper limit of kneading energy is preferably set to be 1000 Wh/kg.

The degree of formation of a composite is conceived to be the ratio of hydrogen bonds between cellulose and the other component. As the formation of a composite proceeds, the ratio of hydrogen bonds increases and the effect of the present invention improves. Furthermore, if formation of a composite proceeds, the median size of colloidal cellulose composites contained in a cellulose composite increases.

In obtaining the cellulose composite of the present invention, when the kneaded mixture obtained in the kneading step mentioned above is dried, a known drying method such as a shelf-stage drying, mist drying, belt drying, fluid-bed drying, lyophilization and a microwave drying can be used. When a kneaded mixture is subjected to a drying step, it is preferable that a kneaded mixture is subjected to a drying step without adding water while maintaining the solid content concentration from the kneading step.

The moisture content of a cellulose composite after drying is preferably 1 to 20 mass %. If the moisture content is 20% or less, problems of e.g., stickiness and decay, and a problem in transportation and carriage cost rarely occur. The moisture content is more preferably 15% or less and particularly preferably 10% or less. Furthermore, if the moisture content is 1% or more, dispersibility is not deteriorated due to overdrying. The moisture content is more preferably 1.5% or more.

For marketing a cellulose composite, powder form is easily handled. Therefore, the dried cellulose composite is preferably pulverized into powder. However, when spray drying is employed as a drying method, drying and powderization can be simultaneously carried out. In this case, pulverization is not necessary. For pulverizing the dried cellulose composite, a known means such as a cutter mill, a hammer mill, a pin mill and a jet mill can be used. Pulverization is performed to the extent that the pulverized cellulose composite can completely pass through a sieve having an opening of 1 mm, more preferably a sieve having an opening of 425 μm and preferably performed so as to obtain an average particle size (weight average particle size) of 10 to 250 μm. These dried powders form a secondary aggregate by aggregating microparticles of a cellulose composite. When the secondary aggregate is stirred in water, it collapses into cellulose composite microparticles as mentioned above. The apparent weight average particle size of the secondary aggregates refers to a cumulative weight 50% particle size in a particle size distribution obtained by sieving a sample (10 g) by means of a ro-tap system sieve shaker (Sieve shaker A type manufactured by Taira Kosakusho) and a JIS standard sieve (Z8801-1987) for 10 minutes.

When the dried cellulose composite is stirred in water, the composite is easily dispersed to form a stable colloidal dispersion having cellulose homogeneously dispersed and having smooth texture without grainy feeling. Particularly, the cellulose composite forms, in a neutral state, a stable colloidal dispersion without causing aggregation and separation of cellulose and thus exerts an excellent function as a stabilizer, etc.

<High-Level Composite Formation at Low Temperature>

As described above, the cellulose composite of the present invention is preferably obtained by blending, as a polysaccharide, two types of CMC-Na different in viscosity in a predetermined ratio.

On the other hand, in the present invention, even if a single CMC-Na having a low viscosity is used in place of two types of CMC-Na different in viscosity, a cellulose composite having excellent suspension stability can be obtained by further reducing the kneading temperature in the production method mentioned above.

The viscosity of the CMC-Na to be used herein is preferably 100 mPa·s or less, more preferably 90 mPa·s or less, further preferably 70 mPa·s or less, particularly preferably 50 mPa·s or less and most preferably 30 mPa·s or less. The lower limit is preferably 1 mPa·s or more, more preferably 5 mPa·s or more, further preferably 10 mPa·s or more and particularly preferably 20 mPa·s or more.

The viscosity herein is measured in the following manner. First, CMC-Na powder is dispersed in pure water so as to obtain a concentration of 2 mass % by use of a high-shear homogenizer (trade name "Excel auto homogenizer ED-7", manufactured by Nippon Seiki Co., Ltd., treatment conditions: rotation number of 15,000 rpm×5 minutes) to prepare an aqueous solution. Then, three hours (stored at 25° C.) after the dispersion, the resultant aqueous solution is set in B-type viscometer (rotor revolving speed: 60 rpm), allowed to stand still for 60 seconds and rotated for 30 seconds, and then, the viscosity was measured. Note that, the rotor can be appropriately changed depending upon the viscosity.

Furthermore, the lower the kneading temperature, the more preferable since the storage elastic modulus (G') of a composite increases. The kneading temperature is preferably 0 to 50° C., more preferably 40° C. or less, particularly preferably 30° C. or less, further preferably 20° C. or less and most preferably 10° C. or less. When kneading is performed at 20° C. or less, the operation until CMC-Na is swollen with water (from initiation of kneading and the amount of electricity reaches 30 Wh/kg) can be made at room temperature or more.

<Uses>

The cellulose composite of the present invention can be used in various types of food products. Examples of uses include various beverages including tasty beverages such as coffee, tea, powdered green tea, cocoa, sweet red-bean soup and juice, milk beverages such as raw milk, processed milk, *lactobacillus* beverage and soy milk, nutrition enriched beverages such as calcium enriched beverage and dietary fiber containing beverages; edible ices such as ice cream, ice milk, soft cream, milk shake and sherbet; milk products such as butter, cheese, yogurt, coffee whitener, whipping cream, custard cream and pudding; processed fat and oil food products such as mayonnaise, margarine, spread and shortening; seasonings such as soup, stew, sauce, baste and dressing; spice pastes represented by mustard paste; fillings represented by jam and flower paste; gel paste foods such as bean paste and jelly; cereal foods including bread, noodle, pasta, pizza and premix; Japanese and western confectioneries such as candy, cookie, biscuit, pancake, chocolate and rice cake; fish paste products represented by fish sausage and Hanppen; livestock products represented by ham, sausage and hamburger steak; prepared foods such as cream croquette, filling for Chinese food, gratin and dumpling; food delicacies such as salted fish guts and pickles with lees; pet foods; and tubal fluid foods.

In these uses, the cellulose composite of the present invention serves as a base reducing calory, such as a suspension stabilizer, an emulsification stabilizer, a thickening stabilizer, a foam stabilizer, a cloudy agent, a texture-adding agent, a fluidity improver, a shape retaining agent, a syneresis inhibitor, a dough modifier, a powder base, a dietary fiber base and oil and fat alternative. Furthermore, even if the above foods are processed such that they are prepared by different cooking patterns in use such as retort food, powdered food, frozen food, food for microwave meal, the effect of the present invention is exerted. Particularly, the cellulose composite of the present invention functions even in a heating environment and a high concentration environment. In this point, the cellulose composite of the present invention is different from conventional cellulose materials.

A food product using the cellulose composite of the present invention may be prepared by adding a main raw material, if necessary, by blending a flavor, a pH moderator, a thickening stabilizer, salts, saccharides, fats and oil, proteins, an emulsifier, an acidulant and a dye, and applying an operation such as mixing, kneading, stirring, emulsifying and heating by use of the same apparatus as generally used in producing foods.

Particularly, the cellulose composite of the present invention has a high storage elastic modulus (G'). Thus, even if a small amount of cellulose composite is added, the cellulose composite provides excellent suspension stability at a low viscosity. The cellulose composite is particularly preferable as a suspension stabilizer for rich-taste beverages containing a component such as coffee, cocoa and a tea extract in a high concentration.

<Method for Adding Cellulose Composite>

As a method for adding the cellulose composite of the present invention to a food and drink, the following method is mentioned. The cellulose composite of the present invention can be added by dispersing it in water simultaneously with a main raw-material or components such as a coloring agent, a spice, an acidulant and a thickener.

Furthermore, when dry powder of a cellulose composite is dispersed in an aqueous medium, it is preferable that the cellulose composite is once dispersed in water and then added to a desired food form. This is because the suspension stability of the cellulose composite is improved. When the cellulose composite is dry powder, the cellulose composite can be dispersed in water by a method of using a kneading machine including various types of dispersion machines, emulsifiers and grinders usually used in production step of foods. Specific examples of the kneading machine that can be used include various types of mixers such as a propeller stirrer, a high-speed mixer, a homo mixer and a cutter; mills such as a ball mill, a colloidal mill, a beads mill and a grinder (Raikai mixer); dispersers/emulsifiers represented by high-pressure homogenizer such as high pressure homogenizer and a nanomizer; and kneading machines represented by e.g., a planetary mixer, kneader, extruder and turbulizer. The kneading machines may be used in combination of two types or more. Furthermore, dispersion can be easily made if kneading is performed while increasing the temperature.

<Additive Amount to Food and Drink>

The additive amount of cellulose composite to a food and drink is not particularly limited. For example, the additive amount of cellulose composite to beverages such as coffee, cocoa and milk is preferably 0.01 mass % or more. If the additive amount of cellulose composite is 0.01 mass % or more, dispersion and suspension stability increases, excellent emulsion stability and syneresis prevention effect can be obtained. The additive amount of cellulose composite is more preferably 0.05 mass % or more and further preferably 0.1 mass % or more. If the additive amount of cellulose composite is 5 mass % or less, aggregation and separation of the cellulose composite do not occur. Also in view of easy-to-take as a beverage (feeling in the throat, grainy feeling on the tongue), the additive amount is preferably 5 mass % or less.

<Water-Insoluble Component>

The cellulose composite of the present invention is particularly preferable for use in neutral foods and drinks containing water-insoluble components. The water-insoluble component refers to a component not dissolved in water and refers, in the present invention, to a component that can pass through a sieve having an opening of 10 mm, more preferably a sieve with 5 mm opening and further preferably a sieve with 2 mm opening. The water-insoluble component becomes unstable in a neutral condition; however, excellent suspension stability is acquired if the cellulose composite of the present invention is added.

As the water-insoluble component, a component having a density of 1.0 g/mL or more is preferable. Since the density is high, the water-insoluble component is rich in nutrient such as carbohydrate and mineral. The density can be obtained by dispersing a water-insoluble component in ion-exchanged water, centrifugally treating (12000G×60 minutes, where G represents a gravitational acceleration) and thereafter making a calculation based on the ratio of volume increase of the whole dispersion solution and increase of mass (mass increase/volume increase). The higher the density, the easier the nutrient intake. Thus the density is preferably high, more preferably 1.1 g/mL or more, further preferably 1.2 g/mL or more and particularly preferably 1.5 g/mL or more. The upper limit is preferably 3 g/mL or less since the water-insoluble component is easily chewed.

Examples of the water-insoluble component include proteins and fruit pieces contained in cocoa powder, cereal powder, food and drink; *lactobacillus* contained in *lactobacillus* beverages and the like; pulp components and the like contained in vegetable juice beverages; functional food materials having a larger specific gravity than water such as milk calcium, calcium carbonate, magnesium and zinc or salts thereof, beta-glucan and proteins (soybean protein, milk protein, collagen), turmeric and lychee; functional food materials having a smaller specific gravity than water such as ubidecarenone compounds such as coenzyme Q10, omega 3 compounds such as docosahexaenoic acid, eicosapentaenoic acid or esters thereof, and ceramide compounds.

As the water-insoluble component to be used and blended in the present invention, particularly, cereal is preferable.

The additive amount of functional food material as mentioned above varies depending upon the amount of intake of beverages per day and the efficacy of the material; however, a functional food material is preferably added in an amount of 0.01 mass % or more based on the beverage, more preferably 0.05 mass % or more, and further preferably 0.1 mass % or more.

<Viscosity of Beverage>

The viscosity of a beverage of the present invention at 25° C. as measured by B type viscometer is preferably 3 to 700 mPa·s. If the viscosity falls within the range, the agglutination/sedimentation of a component can be suppressed and easy-to-take neutral foods and drinks can be prepared. In view of this, the viscosity is more preferably 10 to 400 mPa·s and further preferably 20 to 200 mPa·s.

<Viscoelasticity of Beverage>

Foods and drinks, medicinal products and industrial products of the present invention contain a cellulose composite and a water-insoluble component in an aqueous medium. As the viscoelasticity of these products, a loss tangent, tan δ (loss elastic modulus G″/storage elastic modulus G′), is 1.5 or more. The higher the loss tangent, the more satisfactory taste and flavor (such as rich-taste) becomes when a beverage and the like is taken. Furthermore, the density of a water-insoluble component is preferably 1.0 g/mL or more.

The loss tangent tan δ herein, can be calculated from a storage elastic modulus G′ and a loss elastic modulus G″ measured by a viscoelasticity measurement apparatus based on dependency of stress of a beverage upon distortion and in accordance with the following expression.

The distortion-dependent stress of the water dispersion is measured by a viscoelasticity measurement apparatus (ARES100FRTN1 type, manufactured by Rheometric Scientific, Inc., geometry: Double Wall Couette type, sweeping is performed at a constant temperature at 25.0° C. and an angular velocity of 20 rad/second within a distortion range of 1 to 794%); a water dispersion is slowly supplied by use of a dropper so as not to destroy a microstructure of a cellulose composite in a beverage and allowed to stand still for 5 minutes and then measurement is initiated by Dynamic Strain mode.

$$\text{loss tangent tan } \delta = \text{loss elastic modulus } G''/\text{storage elastic modulus } G' \quad \text{Expression:}$$

In the present invention, loss tangent tan δ is obtained from the storage elastic modulus and loss elastic modulus corresponding to a distortion of 200% on the distortion-stress curve obtained by the aforementioned measurement. The loss tangent tan δ of the above beverage is preferably 1.6 or more, more preferably 1.7 or more, further preferably 1.8 or more, particularly preferably 1.9 or more and most preferably 2 or more.

Note that, in the present invention, the aqueous medium refers to a medium consisting of water (60 mass % to 100 mass %) and a water soluble organic solvent (0 mass % to 40 wt %), more preferably consisting of water (70 mass % to 100 mass %) and a water soluble organic solvent (0 mass % to 30 wt %), further preferably consisting of water (80 mass % to 100 mass %) and a water soluble organic solvent (0 mass % to 20 wt %) and particularly preferably consisting of water (90 mass % to 100 mass %) and a water soluble organic solvent (0 mass % to 10 wt %). Examples of the water soluble organic solvent include alcohols such as methanol, ethanol, propanol, isopropanol, butanol and pentanol; ketones such as acetone and methylethylketone; and polyethylene glycol. When the water soluble organic solvent is used in food, an alcohol such as ethanol that can be orally ingested can be preferably used. In the case of medicinal products, polyethylene glycol that can improve absorption of a medicinal products, can be preferably used.

<Highly Concentrated Cocoa Beverage>

The cellulose composite of the present invention is preferably used in rich-taste cocoa beverages which is high in cacao concentration. The highly concentrated cocoa beverage herein is characterized in that a cacao content (1.5 to 3.5 mass %) is added to a cocoa beverage. As the cacao content, a cocoa powder, a cacao powder and a cacao extract can be used singly or as a mixture having an arbitrary blending ratio. Particularly, if a cocoa powder having a high oil content (10 mass % or more) is used in combination with cacao butter (0.15 mass % or more), a rich-taste cocoa beverage having flavor and rich body can be obtained. In such a highly concentrated cocoa beverage, problems such as ring-formation phenomena, separation of milk fat and sedimentation tend to occur. However, owing to addition of the cellulose composite of the present invention, these problems are overcome to obtain a cocoa beverage stably providing rich-taste, and generation of aggregated substances can be suppressed even after retort sterilization or UHT sterilization. Furthermore, in cocoa beverages containing at least one milk component selected from the group consisting of milk, concentrated milk, whole powdered milk, powdered skim milk and condensed milk, a cocoa beverage containing the milk components suppressed in generation of aggregated substances even after retort sterilization or UHT sterilization can be provided. The conditions of retort sterilization and UHT sterilization herein are not particularly limited as long as they can be usually used for cocoa beverages containing a milk component. Generally, sterilization is performed within the range of 120° C. to 145° C. for 15 seconds to 60 minutes.

<High Concentration Coffee Beverage>

The cellulose composite of the present invention is suitable for a rich-taste coffee beverage having a high coffee concentration. The coffee beverage having a high coffee concentration herein is preferably a coffee beverage having a coffee content of 10 to 15 mass % in terms of green coffee beans. Furthermore, the extraction rate of coffee beans is preferably 15 to 35% and the coffee concentration (Brix value) of a final coffee beverage is preferably 1.5 to 5.25. As a Brix value, a value obtained by a refractometer (N-10E, manufactured by Atago Co., Ltd.) can be used. Since a final coffee beverage contains e.g., sugar and proteins, the Brix value of coffee itself is determined by conversion based on the Brix value of a coffee extract measured and the additive amount of the extract to a coffee beverage.

Furthermore, as the milk component used herein, milk, concentrated milk, whole powdered milk and powdered skim milk are particularly mentioned. In the present invention, owing to the addition of a highly functional cellulose composite, generation of aggregated substances in a milk component-containing coffee beverage containing a content of coffee component beyond 10 mass % in terms of green beans can be suppressed even after retort sterilization or UHT sterilization. Furthermore, even if a coffee beverage containing at least one milk component selected from the group consisting of milk, concentrated milk, whole powdered milk, powdered skim milk and condensed milk, a milk content containing coffee beverage suppressed from generation of aggregated substances even after retort sterilization or UHT sterilization can be provided. The conditions of the retort sterilization and UHT sterilization herein are not particularly limited as long as they are usually used for a coffee beverage containing a milk component; however, sterilization is generally performed within the range of 120° C. to 145° C. for 15 seconds to 60 minutes.

<Highly Concentrated Tea Beverage>

The cellulose composite of the present invention is suitable for a rich-taste tea beverage having a high tea concentration. The tea beverage having a high tea concentration herein refers to a tea beverage having a caffeine content of 10 mg or more per tea beverage (100 mL), when the caffeine concentration of tea beverage which is a tea extract is measured. The tea beverages, from which caffeine is extracted in a high concentration, are preferable since they contain polyphenols such as catechin and tannin in large amounts and thus an antioxidant effect, a sterilization effect and a physical condition improving effect can be obtained by drinking these. In addition, such teas visually emit a vivid color intrinsic to tea such as green and brown. The caffeine herein serves as an index for the concentration of these tea extracts. Accordingly, the caffeine concentration is more preferably 15 mg or more per beverage (100 mL), further preferably 20 mg or more, particularly preferably 30 mg or more and most preferably 40 mg or more. The higher the concentration of a tea extract, the stronger the bitter taste and the harder the tea is taken. Thus, the upper limit is 100 mg or less.

The term of the tea herein refers to an extract of tea, which is obtained by drying leaves and stems of plants to obtain raw materials and extracting components from the raw materials with water or hot water. Leaves and stems of an evergreen tree belongs to *Camellia Camellia* are preferably used for a tea plant (scientific name: *Camellia sinensis*). These plant raw-materials can be classified in accordance with the processing method as follows. Green tea (non-fermented tea) is a tea obtained without oxidative fermentation; white tea (weakly fermented tea) is a tea obtained by shortly applying oxidative fermentation; and blue tea (semi-fermented tea) is a tea obtained by applying oxidative fermentation to some extent, in which oolong tea is classified. Red tea (completely fermented tea or fully fermented tea) is a tea obtained by complete oxidative fermentation; yellow tea (weak afterfermented tea) is a tea obtained by applying the same process as in white tea and thereafter weakly applying oxidative fermentation; and black tea (afterfermented tea) is a tea obtained by fermenting green tea in a general sense with *Aspergillus oryzae*, in which Pu-erh tea is classified. Among them, green tea, blue tea and red tea are preferably used for the tea beverage in the present invention in view of taste and flavor and content of a component good for heath.

Pigments extracted from these teas more or less fade away by sterilization, which is performed for storing beverages for a long time; however, the cellulose composite of the present invention has an effect of suppressing color fading during sterilization due to a heat shield effect of CMC-Na radially extending from a crystalline cellulose. The content of a crystalline cellulose composite in a highly concentrated tea beverage is preferably 0.05 mass % or more, more preferably 0.1 mass % or more, further preferably 0.15 mass % or more, particularly preferably 0.2 mass % or more and most preferably 0.3 mass % or more. The larger the content of the crystalline cellulose composite, the more the color-fading prevention effect and suspension stabilization effect can be obtained; however, when the concentration becomes high, it becomes difficult to swallow. For the reason, the upper limit is preferably 5 mass % or less, more preferably 3 mass % or less, further preferably 2 mass % or less and particularly preferably 1 mass %.

To reduce bitter taste, a milk component including animal milk such as cow milk and goat milk and vegetable milk such as soy milk is preferably blended to the beverage of the present invention. The concentration of a milk component can be determined based on the amount of protein in a beverage. The amount of protein is preferably 0.1 g or more per beverage (100 mL), more preferably 0.2 g or more per beverage (100 mL), further preferably 0.3 g or more, particularly preferably 0.5 g or more and most preferably 1 g or more. The upper limit is set within the range not damaging taste and flavor intrinsic to tea, preferably 3 g or less and more preferably 2 g or less.

<Meal Alternative Beverage>

The meal alternative beverage refers to a beverage rich in nutrients, which contains beans and cereals in an aqueous medium and serves as an alternative and a supplement for a meal such as breakfast. The crystalline cellulose composite of the present invention is excellent in suspension stability for a high-concentration carbohydrate and protein and in preventing color fading, and thus it is suitably used for the meal alternative beverage.

As the beans and cereals contained in the meal alternative beverage of the present invention, the following ones are mentioned. As the beans, pulverized products or paste of seeds and fruits of plants of the legume family are preferably blended. As the seeds or fruits derived from plants of the legume family, soy bean, azuki, common bean, lima bean, pea, scarlet runner, broad bean, cherry bean, chick-pea, greengram, lentil, locust bean, peanut, cluster bean, jack bean and pigeon pea can be used. As the seeds or fruits except the legume family, coffee bean (Rubiaceae family), cacao (Sterculiaceae or Malvaceae family) and Mexican jumping bean (Euphorbia family) can be used.

The cereal herein refers to pulverized products or paste of seeds or fruits of the gramineous plant, wheat and analogous grain plants. Examples of grains of the gramineous plant include *sativa* (Asian rice), *japonica* (Japan), *javanica* (Jave), *indica* (India), *glaberrima* (African rice), *nerica* (hybrid between Asian rice and African rise) and corn (Corn). Examples of wheat include barley (barley), sticky wheat (a sticky kind of barley), hull-less barley (variant of barley), wheat (wheat), rye (rye), oat, oat wheat (oat), Job's tear (not seed but fruit), millet, Italian millet, Japanese millet, corn (Indian millet, kaoliang, sorghum), American millet, pearl millet, Kedong millet, Indian rice (between a wild plant and cultivated plant). Furthermore, examples of the analogous grains include buckwheat, rye buckwheat, amaranth (*amaranthus, amaranthus caudatus*) and *quinoa*.

Since the cellulose composite of the present invention has excellent suspension stability, it is possible to produce meal alternative beverages containing these beans and grains rich in nutrient in high concentrations.

As the beans suitable for the meal alternative beverage, soy bean, azuki, common bean, pea, broad bean, greengram and peanut are preferable and soy bean, azuki and peanut are more preferable.

As the grains suitable for the meal alternative beverage, *sativa* (Asian rice), *japonica* (Japan), *javanica* (Jave), indica (India) and corn are preferable. As wheats, barley (barley), wheat (wheat), rye (rye) and oat wheat (oat) are preferable. As analogous grains, buckwheat is preferable. More preferably *sativa* (Asian rice), *javanica* (Jave), indica (India), corn (corn), barley (barley), rye (rye) and oat wheat (oat) are used. Since these are rich in dietary fiber and minerals in addition to a carbohydrate, they are preferably used as a meal alternative.

The additive amount of the beans and cereals mentioned above, varies depending upon the amount of intake per day and efficacy of nutrition of the material. The beans and cereals are preferably added in an amount of 1 mass % or more relative to a beverage, more preferably 2 mass % or more, further preferably 3 mass % or more and particularly preferably 5 mass % or more. The upper limit of the content, which varies depending upon the processing method for these and the viscosity of a final beverage, is preferably 20 mass % or less. In view of easiness in drinking, the upper limit is preferably 10 mass % or less.

Pigments of these beans and cereals more or less fade away by sterilization, which is performed for storing beverages for a long time; however, the cellulose composite of the present invention has an effect of suppressing color fading during sterilization due to a heat shield effect of CMC-Na radially extending from a crystalline cellulose. The content of a crystalline cellulose composite in a meal alternative beverage is preferably 0.05 mass % or more, more preferably 0.1 mass % or more, further preferably 0.15 mass % or more, particularly preferably 0.2 mass % or more and most preferably 0.3 mass % or more. The larger the content of the crystalline cellulose composite, the more the color-fading prevention effect and suspension stabilization effect can be obtained; however, when the concentration becomes high, it becomes difficult to swallow. For the reason, the upper limit is preferably 5 mass % or less, more preferably 3 mass % or less, further preferably 2 mass % or less and particularly preferably 1 mass %.

To reduce bitter taste, a milk component including animal milk such as cow milk and goat milk and vegetable milk such as soy milk is preferably blended to the beverage of the present invention. The concentration of a milk component can be determined based on the amount of protein in a beverage. The amount of protein is preferably 0.1 g or more per beverage (100 mL), more preferably 0.2 g or more per beverage (100 mL), further preferably 0.3 g or more, particularly preferably 0.5 g or more and most preferably 1 g or more. The upper limit is set within the range not damaging taste and flavor of materials, preferably 3 g or less, and more preferably 2 g or less.

<Use Other than Food>

The cellulose composite of the present invention is significantly improved in colloid dispersibility and can be applied to, other than foods, medicinal products such as a syrup agent, a liquid agent and an ointment; cosmetics such as a lotion, an emulsion and a cleaner; raw materials for cleaners and treatment agents for food and industrial use, raw materials for detergents for household use (clothes, a kitchen, a house, tableware, etc.), paints, pigments, ceramics, water based latex, agents for emulsification (polymerization), agents for agriculture, agents for fiber processing (refinement agent, dyeing assistant, softener, water repellent, soil-release finishing agents, concrete admixtures, printing inks, lubrication oils, antistatic agents, antifog additives, lubricants, dispersants, deinking agents, etc. Among these, particularly, in a composition of an aqueous suspension state containing a water-insoluble component, a stable dispersion state can be maintained without causing aggregation, separation, syneresis and sedimentation. Furthermore, the cellulose composite is significantly improved in performance as a stabilizer and a problem of grainy feeling can be overcome by its smooth feeling on the tongue and body. Therefore, the cellulose composite can be used in a wide variety of foods other than those described above.

EXAMPLES

The present invention is described by way of the following Examples. However, these should not be construed as limiting the scope of the present invention.

<Average Polymerization Degree of Cellulose>

The average polymerization degree of cellulose was measured by a reduced specific viscosity method using a copper ethylene diamine solution, which is defined in the crystalline cellulose identification test (3) of "the 14th edition of the Japanese Pharmacopoeia" (published by Hirokawa Shoten K.K.).

<Viscosity of Sodium Carboxymethylcellulose (CMC-Na)>

(1) CMC-Na powder was dispersed in pure water in a concentration of 2 mass % by use of a high-shear homogenizer (trade name "Excel auto homogenizer ED-7" manufactured by Nippon Seiki Co., Ltd., treatment conditions: rotation number of 15,000 rpm×5 minutes) to prepare an aqueous solution.

(2) Three hours after the dispersion (stored at 25° C.), the obtained aqueous solution was set in B-type viscometer (rotor revolving speed: 60 rpm), allowed to stand still for 60 seconds and rotated for 30 seconds, and then, a viscosity was measured. Note that, the rotor can be appropriately changed depending upon the viscosity.

<Viscosity of Water Dispersion of Cellulose Composite>

A cellulose composite was dispersed in pure water by use of a high-shear homogenizer (trade name "Excel auto homogenizer ED-7" manufactured by Nippon Seiki Co., Ltd., treatment conditions: rotation number of 15,000 rpm×5 minutes) to prepare 1.0 mass % pure water dispersion. Three hours after the dispersion (stored at 25° C.), the obtained water dispersion was set in B-type viscometer (rotor revolving speed: 60 rpm), allowed to stand still for 30 seconds and rotated for 30 seconds, and then a viscosity was measured. Note that, the rotor can be appropriately changed depending upon the viscosity. The rotors used herein were as follows: 1 to 20 mPa·s: BL type, 21 to 100 mPa·s: No. 1, 101 to 300 mPa·s: No. 2, 301 mPa·s or more: No. 3).

<Molecular-Weight Distribution of CMC-Na>

(1) First, CMC-Na was dissolved in a 0.05 mol/L aqueous sodium hydroxide solution in a concentration of 0.5 mass %.

(2) Then, the CMC-Na solution (5 µL) was injected in high performance liquid chromatographic apparatus (trade name LC-20A type manufactured by Shimadzu Corporation), to which a single column (trade name TSK-GEL G5000PW type (7.8 mm×30 cm), manufactured by Tosoh Corporation) and two columns (trade name TSK-GEL G3000 PWXL type (7.8 mm×30 cm)) are connected in line. Measurement is performed by supplying an aqueous 0.05 mol/L aqueous sodium hydroxide solution as a mobile phase, at a flow rate of 1 mL/minute and setting a column temperature at 30° C. Detection is made by a UV detector (wavelength: 210 nm).

(3) From the obtained chromatogram, the number of peaks was visually counted.

Figure 3:
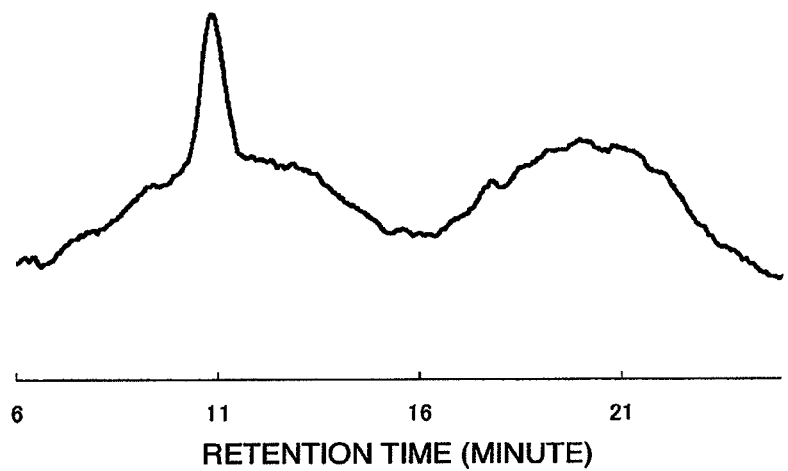
FIG. 3 shows a GPC chromatogram of sodium carboxymethylcellulose used for production in Examples 1, 3 to 5.

FIG. 3 shows a GPC chromatogram of CMC-Na used for production of Examples 1, 3 to 5. Two peaks (bimodal), i.e., a peak derived from CMC-Na of a low molecular weight (viscosity 25 mPa·s) at a retention time of 16 to 24 minutes and a peak derived from CMC-Na of a high molecular weight (viscosity 620 mPa·s) at 6 to 16 minutes were detected. Note that, the peak detected at 11 minutes is an unidentified peak, which is not derived from CMC-Na.

Figure 4:
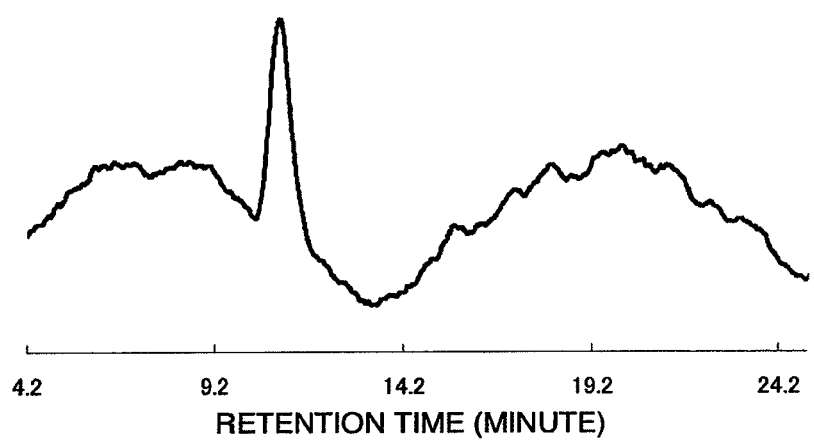
FIG. 4 shows a GPC chromatogram of sodium carboxymethylcellulose used for production in Example 2.

FIG. 4 shows a GPC chromatogram of CMC-Na used for production of Example 2. Two peaks (bimodal), i.e., a peak derived from CMC-Na of a low molecular weight (viscosity 25 mPa·s) at a retention time of 14 to 24 minutes and a peak derived from CMC-Na of a high molecular weight (viscosity 7000 mPa·s) at 4 to 13 minutes were detected. Note that, the peak detected at 11 minutes is an unidentified peak, which is not derived from CMC-Na.

Figure 5:
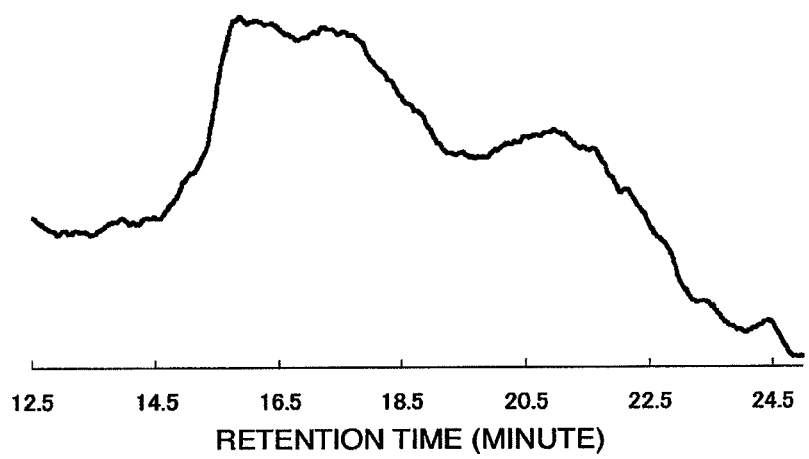
FIG. 5 shows a GPC chromatogram of sodium carboxymethylcellulose used for production in Example 8.

FIG. 5 shows a GPC chromatogram of CMC-Na used for production of Example 8. Two peaks (bimodal), i.e., a peak derived from CMC-Na of a low molecular weight (viscosity 50 mPa·s) at a retention time of 19 to 23 minutes and a peak derived from CMC-Na of a high molecular weight (viscosity 500 mPa·s) at 14 to 19 minutes were detected.

<Substitution Degree of CMC-Na>

(1) CMC-Na (anhydride) (0.5 g) was accurately weighed, wrapped with a filter and baked in a magnetic crucible into ash. After cooling, this was transferred to a 500 mL beaker. To the beaker, water (about 250 mL) and 0.05 M sulfuric acid (35 mL) were added and the obtained mixture was boiled for 30 minutes. The resultant mixture was cooled and a phenolphthalein indicator was added. Excessive acid was neutralized by back titration with 0.1 M potassium hydroxide. The substitution degree was calculated by the following expressions.

$$A=((af-bf1)/\text{sample anhydride (g)})-\text{alkali level (or +acid level)}$$

$$\text{Substitution degree}=(162 \times A)/(10000-80A)$$

where
A: Amount of 0.05 M sulfuric acid (mL) consumed by alkali per sample (1 g)
a: Use amount of 0.05 M sulfuric acid (mL)
f: Titer of 0.05 M sulfuric acid
b: Titer (mL) of 0.1 M potassium hydroxide
f1: Titer of 0.1 M potassium hydroxide
162: Molecular weight of glucose
80: Molecular weight of $CH_2COONa-H$ Method of Measuring Alkali Level (or Acid Level):

A sample (anhydride) (1 g) was accurately weighed in a 300 mL-flask. To this flask, water (about 200 mL) was added to dissolve the sample. To this, 0.05 M sulfuric acid (5 mL) was added and the mixture was boiled for 10 minutes and cooled. To this resultant mixture, a phenolphthalein indicator was added and titrated with 0.1 M potassium hydroxide (S mL). At the same time, a blank test was performed (B mL). The alkali level was calculated in accordance with the following expression.

$$\text{Alkali level}=((B-S) \times f)/\text{sample anhydride (g)}$$

where
f: Titer of 0.1 M potassium hydroxide. If a value of $\{(B-S) \times f\}$ was a negative value $(-)$, the alkali level was regarded as an acid level.

<Method for Measuring Storage Elastic Modulus of Cellulose Composite>

(1) A cellulose composite was dispersed in pure water by a high-shear homogenizer (trade name "Excel autohomogenizer ED-7" manufactured by Nippon Seiki Co., Ltd., treatment conditions: rotation number 15,000 rpm×5 minutes) to prepare a pure water dispersion of 1.0 mass % in concentration. Thereafter, the resultant water dispersion was allowed to stand still at room temperature for 3 days.

(2) The distortion dependent stress of the water dispersion was measured by a viscoelasticity measuring apparatus (ARES100FRTN1 type, manufactured by Rheometric Scientific, Inc., geometry: Double Wall Couette type, distortion was swept in the range of 1 to 794%). In the present invention, as storage elastic modulus (G'), a value corresponding to a distortion of 20% on the distortion-stress curve obtained in the aforementioned measurement was used.

<Content of Colloidal Cellulose Composite in Cellulose Composite>

(1) A cellulose composite was suspended in pure water in a concentration of 0.5 mass % and the resultant suspension was dispersed by a high-shear homogenizer (trade name "Excel autohomogenizer ED-7", manufactured by Nippon Seiki Co., Ltd., treatment conditions: rotation number 15,000 rpm×5 minutes).

(2) The dispersion solution was centrifugally separated by a centrifuge (trade name "6800 type centrifuge" rotor-type RA-400, manufactured by KUBOTA Corporation, treatment conditions: centrifugal force of 39200 $m^2$/s) for 10 minutes. The supernatant was taken and further centrifugally treated at 116000 $m^2$/s for 45 minutes.

(3) After the centrifugation, the supernatant was fed into a glass weighing bottle and dried at 60° C. for 15 hours and thereafter at 105° C. for 2 hours. After a constant weight was obtained in a desiccator, the weight was measured. Separately, non-centrifuged water dispersion was dried in the same manner and the weight was measured. From the results, the mass percentage of the cellulose solid content remaining in the supernatant was obtained in accordance with the following expression.

Computation expression of content of colloidal cellulose composite: (solid content of the supernatant (50 g))/(solid content of non-centrifuged water dispersion (50 g))×100

<Median Size of Colloidal Cellulose Composite Measured by Dynamic Light Scattering Method>

(1) A cellulose composite was suspended in pure water in a concentration of 0.5 mass % and dispersed by a high-shear homogenizer (trade name "Excel auto homogenizer ED-7", manufactured by Nippon Seiki Co., Ltd., treatment conditions: rotation number of 15,000 rpm×5 minutes) and centrifugally separated by a centrifuge (trade name "6800 type centrifuge" rotor-type RA-400, manufactured by KUBOTA Corporation, treatment conditions: centrifugal force of 39200 $m^2$/s) for 10 minutes. The supernatant was collected and further centrifugally treated at 116000 $m^2$/s for 45 minutes, and the resultant supernatant was collected.

(2) The supernatant was placed in a 50-mL (volume) sample tube made of PP and ultrasonically treated by an ultrasonic cleaner (an ultrasonic cleaner, trade name: AUC-1L type manufactured by AS ONE Corporation) for 10 minutes.

(3) Thereafter, a particle size distribution (frequency distribution of scattering intensity versus particle size value) was measured by a zeta potential-particle size measurement system (trade name "ELSZ-2" (batch cell), manufactured by Otsuka Electronic Co., Ltd.). The median size herein refers to a particle size value (μm) corresponding to a cumulative 50% scattering intensity in the frequency distribution.

<Median Size of Colloidal Cellulose Composite Measured by the Laser Diffraction/Scattering Method (Particle Size of Cellulose Core of Cellulose Composite)>

(1) A cellulose composite was suspended in pure water in a concentration of 0.5 mass %, dispersed by a high-shear homogenizer (trade name "Excel auto homogenizer ED-7", manufactured by Nippon Seiki Co., Ltd., treatment conditions: rotation number of 15,000 rpm×5 minutes) and centrifugally separated by a centrifuge (trade name "6800 type centrifuge" rotor-type RA-400, manufactured by KUBOTA Corporation, treatment conditions: centrifugal force of 39200 $m^2$/s) for 10 minutes. The supernatant was collected and further centrifugally treated at a rate of 116000 $m^2$/s for 45 minutes and the resultant supernatant was collected.

(2) The supernatant was measured by a laser diffraction/scattering particle size distribution meter (trade name "LA-910" manufactured by Horiba, Ltd. ultrasonic treatment: 1 minute, refractive index: 1.20). In the obtained volume frequency particle size distribution, the cumulative 50% particle size (a volume average particle size) was obtained.

<Median Size of Coarse Particles Measured by the Laser Diffraction/Scattering Method>

(1) A cellulose composite was suspended in pure water in a concentration of 0.5 mass %, dispersed by a high-shear homogenizer (trade name "Excel auto homogenizer ED-7", manufactured by Nippon Seiki Co., Ltd., treatment conditions: rotation number of 15,000 rpm×5 minutes).

(2) The dispersion solution was measured as it is by a laser diffraction/scattering particle size distribution meter (trade name "LA-910" manufactured by Horiba, Ltd. ultrasonic treatment: 1 minute, refractive index: 1.20). In the obtained volume frequency particle size distribution, the cumulative 50% particle size (volume average particle size) was obtained.

<Shape of Cellulose Particle (L/D)>

A cellulose composite was suspended in pure water in a concentration of 1 mass % and dispersed by a high-shear homogenizer (trade name "Excel autohomogenizer ED-7" manufactured by Nippon Seiki Co., Ltd., treatment conditions: rotation number 15,000 rpm×5 minutes). The resultant water dispersion was diluted with pure water up to 0.1 mass % and a single drop was casted on mica by use of a dropper. Excessive moisture content was blown out by an air duster and dried in the air to prepare a sample. An image was measured by an atomic force microscope (apparatus of Nano Scope IV MM, manufactured by Digital Instruments, scanner EV, measuring mode Tapping, probe NCH type silicon single crystal probe). Based on the obtained image, the major axis (L) and the minor axis (D) of particles having a major axis (L) of 2 μm or less were measured. The shapes of cellulose particles, which are defined by the ratio of (L/D), were calculated as an average value of 100 to 150 particles.

<Structure of Cellulose Composite: Observation of Spread of a Polysaccharide from Cellulose>

A cellulose composite was dispersed in pure water by use of a high-shear homogenizer (trade name "Excel auto homogenizer ED-7", manufactured by Nippon Seiki Co., Ltd., treatment conditions: rotation number of 15,000 rpm×5 minutes, total amount 300 g) to prepare a 1.0 mass % pure water dispersion. The obtained water dispersion was allowed to stand still for 3 days or more at room temperature. Thereafter, the water dispersion was diluted 20 folds with pure water to prepare a sample solution. An aliquot (5 μl) was slowly suctioned so as not to destroy the microstructure of a water dispersion by use of a dropper and slowly added dropwise on a mica cut piece of 1 cm×1 cm. Extra moisture was blown away by an air duster and the sample fixed on the mica was observed by AFM (scanning probe microscope SPM-9700 manufactured by Shimadzu Corporation, phase mode, a probe OMCL-AC240TS manufactured by Olympus Corporation was used). In the observed image, it was found that a cellulose particle is a rod particle having a height of 2 nm or more, and that a polysaccharide having a height of less than 2 nm radially extends from the cellulose particle peripherally (FIG. 1: an AFM image of cellulose composite D obtained in Example 4).

Example 1

Commercially available DP pulp was cut into pieces and hydrolyzed in 2.5 mol/L hydrochloric acid at 105° C. for 15 minutes, washed with water and then filtrated to prepare a wet-cake like cellulose having a solid content of 50 mass % (average polymerization degree was 220).

Next, wet-cake like cellulose, commercially available CMC-Na (the viscosity of 2% solution: 620 mPa·s, substitution degree: 0.7 to 0.8) as Component A, and commercially available CMC-Na (the viscosity of 2% solution: 25 mPa·s, substitution degree: 0.7 to 0.8) as Component B were prepared. They were put in a planetary mixer (5DM-03-R, manufactured by Shinagawa Machinery Works Co., Ltd., agitating blade was hook type) such that the mass ratio of cellulose (hereinafter referred to as MCC)/CMC-Na (Component A+Component B) became 90/10 (where constitution of CMC-Na: Component A/Component B=50/50) and water was added so as to obtain a solid content of 45 mass %.

Thereafter, the mixture was kneaded at 126 rpm to obtain cellulose composite A. The kneading energy was controlled according to kneading time in the planetary mixer and actual measurement value thereof was 390 Wh/kg. As the kneading temperature, the temperature of the kneaded mixture was directly measured by a thermocouple. The kneading temperature was 20 to 40° C. throughout the kneading.

The storage elastic modulus (G') of the resultant cellulose composite A was 5.5 Pa. Furthermore, Particle L/D of the cellulose composite A was 1.6; the content of the colloidal cellulose composite was 78 mass %; the median size measured by a dynamic light scattering method of the colloidal cellulose composite was 2.5 μm; the median size measured by a laser diffraction/scattering method was 0.13 μm; and the median size of coarse particles was 6.5 μm. The viscosity of a water dispersion of the cellulose composite was 383 mPa·s.

The results are shown in Table 1.

Example 2

Using chipped commercially available DP pulp, cellulose was hydrolyzed in the same manner as in Example 1. Subsequently, wet-cake like cellulose (average polymerization degree: 220), commercially available CMC-Na (the viscosity of 2% solution: 7000 mPa·s, substitution degree: 0.7 to 0.8) as Component A, and commercially available CMC-Na (the viscosity of 2% solution: 25 mPa·s, substitution degree: 0.7 to 0.8) as Component B were prepared. MCC and Components A and B were added such that the mass ratio of MCC/CMC-Na (Component A+Component B) became 52/48 (where constitution of CMC-Na: Component A/Component B=10/90), and water was added so as to obtain a solid content of 45 mass %. The mixture was kneaded in the same manner as in Example 1 to obtain cellulose composite B. Kneading energy was controlled depending upon the kneading time of a planetary mixer and an actual value thereof was 220 Wh/kg. The kneading temperature of the kneading mixture, which was directly measured by use of a thermocouple, was 20 to 40° C. throughout the kneading.

The storage elastic modulus (G') of the obtained cellulose composite B was 1.4 Pa; particle L/D was 1.6; the content of the colloidal cellulose composite was 69 mass %; the median size measured by a dynamic light scattering method of the colloidal cellulose composite was 1.2 μm; the median size measured by a laser diffraction/scattering method was 0.13 μm; and the median size of coarse particles was 9.3 μm. The viscosity of a water dispersion of the cellulose composite was 252 mPa·s.

The results are shown in Table 1.

Example 3

Using chipped commercially available DP pulp, cellulose was hydrolyzed in the same manner as in Example 1. Subsequently, wet-cake like cellulose (average polymerization degree: 220), commercially available CMC-Na (the viscosity of 2% solution: 620 mPa·s, substitution degree: 0.7 to 0.8) as Component A, and commercially available CMC-Na (the viscosity of 2% solution: 25 mPa·s, substitution degree: 0.7 to 0.8) as Component B were prepared. MCC and Components A and B were added such that the mass ratio of MCC/CMC-Na (Component A+Component B) became 80/20 (where constitution of CMC-Na: Component A/Component B=40/60), and water was added so as to obtain a solid content of 40 mass %. The mixture was kneaded in the same manner as in Example 1 to obtain cellulose composite C. Kneading energy was controlled depending upon the kneading time of a planetary mixer and an actual value thereof was 190 Wh/kg. The kneading temperature was controlled by cooling a jacket and the temperature of the kneading mixture, which was directly measured by use of a thermocouple, was 20 to 60° C. throughout the kneading.

The storage elastic modulus (G') of the obtained cellulose composite C was 2.3 Pa; particle L/D was 1.6; the content of the colloidal cellulose composite was 67 mass %; the median size of the colloidal cellulose composite measured by a dynamic light scattering method was 1.1 μm; the median size measured by a laser diffraction/scattering method was 0.13 μm; and the median size of coarse particles was 8.2 μm. The viscosity of a water dispersion of the cellulose composite was 182 mPa·s.

The results are shown in Table 1.

Example 4

Using commercially available KP pulp, cellulose was hydrolyzed in the same manner as in Example 1. Subsequently, wet-cake like cellulose (average polymerization degree: 220), commercially available CMC-Na (the viscosity of 2% solution: 620 mPa·s, substitution degree: 0.7 to 0.8) as Component A, and commercially available CMC-Na (the viscosity of 2% solution: 25 mPa·s, substitution degree: 0.7 to 0.8) as Component B were prepared. MCC and Components A and B were added such that the mass ratio of MCC/CMC-Na (Component A+Component B) became 90/10 (where constitution of CMC-Na: Component A/Component B=40/60), and water was added so as to obtain a solid content of 50 mass %. The mixture was kneaded in the same manner as in Example 1 to obtain cellulose composite D. Kneading energy was controlled depending upon the kneading time of a planetary mixer and an actual value thereof was 100 Wh/kg. The kneading temperature was controlled by cooling a jacket and the temperature of the kneading mixture, which was directly measured by use of a thermocouple, was 20 to 65° C. throughout the kneading.

The storage elastic modulus (G') of the obtained cellulose composite D was 2.5 Pa; particle L/D was 1.6; the content of the colloidal cellulose composite was 72 mass %; the median size measured by a dynamic light scattering method of the colloidal cellulose composite was 1.2 μm; the median size measured by a laser diffraction/scattering method was 0.13 μm; and the median size of coarse particles was 9.1 μm. The viscosity of a water dispersion of the cellulose composite was 220 mPa·s.

The results are shown in Table 1.

Example 5

Using chipped commercially available DP pulp, cellulose was hydrolyzed in the same manner as in Example 1. Subsequently, wet-cake like cellulose (average polymerization degree: 220), commercially available CMC-Na (the viscosity of 2% solution: 620 mPa·s, substitution degree: 0.7 to 0.8) as Component A, and commercially available CMC-Na (the viscosity of 2% solution: 25 mPa·s, substitution degree: 0.7 to 0.8) as Component B were prepared. Other than MCC and CMC-Na, xanthan gum as a water soluble gum and dextrin as a hydrophilic substance were blended. MCC, Components A and B, xanthan gum and dextrin were added such that the mass ratio of MCC/CMC-Na (Component A+Component B)/xanthan gum/dextrin became 70/5/5/20 (where constitution of CMC-Na: Component A/Component B=50/50), and water was added so as to obtain a solid content of 45 mass %. The mixture was kneaded in the same manner as in Example 1 to obtain cellulose composite E. Kneading energy was controlled depending upon the kneading time of a planetary mixer and an actual value thereof was 80 Wh/kg. The kneading temperature was controlled by cooling a jacket and the temperature of the kneading mixture, which was directly measured by use of a thermocouple, was 20 to 65° C. throughout the kneading.

The storage elastic modulus (G') of the obtained cellulose composite E was 1.2 Pa; particle L/D was 1.6; the content of the colloidal cellulose composite was 75 mass %; the median size measured by a dynamic light scattering method of the colloidal cellulose composite was 0.95 μm; the median size measured by a laser diffraction/scattering method was 0.16 μm; and the median size of coarse particles was 8.5 μm. The viscosity of a water dispersion of the cellulose composite was 140 mPa·s.

The results are shown in Table 1.

Example 6

Using chipped commercially available DP pulp, cellulose was hydrolyzed in the same manner as in Example 1. Subsequently, wet-cake like cellulose (average polymerization degree: 220) and commercially available CMC-Na (the viscosity of 2% solution: 25 mPa·s, substitution degree: 0.7 to 0.8) as Component B were prepared. Component A was not added. MCC and CMC-Na (Component B) were added such that the mass ratio of MCC/CMC-Na (Component B) became 90/10 (where constitution of CMC-Na: Component A/Component B=0/100), and water was added so as to obtain a solid content of 45 mass %. The mixture was kneaded in the same manner as in Example 1 to obtain cellulose composite F.

Kneading energy was controlled depending upon the kneading time of a planetary mixer, an actual value thereof was 200 Wh/kg. The kneading temperature was controlled by cooling a jacket and measured by use of a thermocouple. The mixture was kneaded at 50° C. or less until the kneading energy reached 30 Wh/kg. Thereafter, the kneaded mixture was cooled by cooling the jacket and the temperature of the kneaded mixture was 15° C. or less throughout the kneading.

The storage elastic modulus (G') of the obtained cellulose composite F was 1.0 Pa; particle L/D was 1.6; the content of the colloidal cellulose composite was 78 mass %; the median size measured by a dynamic light scattering method of the colloidal cellulose composite was 0.85 μm; the median size measured by a laser diffraction/scattering method was 0.13 μm; and the median size of coarse particles was 7.8 μm. The viscosity of a water dispersion of the cellulose composite was 175 mPa·s.

The results are shown in Table 1.

Comparative Example 1

Using chipped commercially available DP pulp, cellulose was hydrolyzed in the same manner as in Example 1.

Subsequently, wet-cake like cellulose (average polymerization degree: 220) and commercially available CMC-Na (the viscosity of 2% solution: 620 mPa·s, substitution degree: 0.7 to 0.8) as Component A were added without adding Component B such that the mass ratio of MCC/CMC-Na (Component A+Component B) became 90/10 (where constitution of CMC-Na: Component A/Component B=100/0), and water was added so as to obtain a solid content of 37 mass %. The mixture was kneaded in the same manner as in Example 1 to obtain cellulose composite G. Kneading energy was controlled depending upon the kneading time of a planetary mixer and an actual value thereof was 60 Wh/kg. The kneading temperature was controlled by cooling a jacket and the temperature of the kneading mixture, which was directly measured by use of a thermocouple, was 20 to 85° C. throughout the kneading.

The storage elastic modulus (G') of the obtained cellulose composite G was 0.45 Pa; particle L/D was 1.6; the content of the colloidal cellulose composite was 70 mass %; the median size measured by a dynamic light scattering method of the colloidal cellulose composite was 0.81 μm; the median size measured by a laser diffraction/scattering method was 0.13 μm; and the median size of coarse particles was 9.5 μm. The viscosity of a water dispersion of the cellulose composite was 98 mPa·s.

The results are shown in Table 1.

Comparative Example 2

Commercially available DP pulp was cut into pieces and hydrolyzed in 10 mass % hydrochloric acid at 105° C. for 20 minutes. The acid insoluble residue obtained by the hydrolysis was filtrated and washed to prepare a cellulose water dispersion having a solid content of 10 mass % (average polymerization degree was 200). The volume average particle size of the hydrolysis cellulose was 17 μm. The cellulose water dispersion was subjected twice to a pulverizing process performed by a medium stirring wet-process pulverization apparatus (apex mill, AM-1 type, manufactured by Kotobuki Engineering & Manufacturing Co., Ltd.) using zirconia beads having a diameter of 1 mm φ as a medium in the conditions where a stirring blade rotation number was 1800 rpm and a cellulose water dispersion supply amount was 0.4 L/min to obtain micro cellulose paste.

A paste-like micro cellulose/CMC-Na (substitution degree: 0.90, viscosity: 7 mPa·s) were weighed so as to satisfy a mass ratio of 80/20. To this mixture, pure water was added so as to satisfy a total solid content concentration of 11 mass %. The resultant mixture was dispersed by a TK homo mixer (MARKII, manufactured by Tokushu Kika Kogyo Co., Ltd.) at 8,000 rpm for 20 minutes to prepare a paste-like water dispersion (as the kneading energy was calculated from power consumption of the apex mill and TK homogenizer and a treatment amount, it was 30 Wh/kg. The kneading temperature, which was measured in the same manner as in Example 1, was 20 to 60° C. throughout the kneading and the achieving temperature was 50 to 60° C.).

The water dispersion was dried by a drum dryer (KDD-1 type, manufactured by Kusunoki Kikai Seisakusho) at a water vapor pressure of 2 Kg/cm$^2$, a rotation number of 0.6 rpm, scratched out by a scraper and roughly pulverized by a flush mill (manufactured by Fuji Paudal Co., Ltd.) to obtain thin slice or scale like cellulose composite H. The kneading energy was 0.03 kWh/kg.

The storage elastic modulus (G') of the obtained cellulose composite H was 0.38 Pa; particle L/D was 1.3; the content of the colloidal cellulose composite was 91 mass %; the median size measured by a dynamic light scattering method of the colloidal cellulose composite was 0.65 μm; the median size measured by a laser diffraction/scattering method was 0.11 μm; and the median size of coarse particles was 3.4 μm. The viscosity of a water dispersion of the cellulose composite was 80 mPa·s.

The results are shown in Table 1.

Comparative Example 3

Using chipped commercially available DP pulp, cellulose was hydrolyzed in the same manner as in Example 1. Subsequently, wet-cake like cellulose (average polymerization degree: 220) and commercially available CMC-Na (the viscosity of 2% solution: 7 mPa·s, substitution degree: 0.7 to 0.8) as Component B were added without adding Component A such that the mass ratio of MCC/CMC-Na (Component B) became 90/10 (where constitution of CMC-Na: Component A/Component B=0/100), and water was added so as to obtain a solid content of 40 mass %. The mixture was kneaded in the same manner as in Example 1 to obtain cellulose composite I. Kneading energy was controlled depending upon the kneading time of a planetary mixer and an actual value thereof was 60 Wh/kg. The kneading temperature was controlled by cooling a jacket and the temperature of the kneading mixture, which was directly measured by use of a thermocouple, was 20 to 85° C. throughout the kneading.

The storage elastic modulus (G') of the obtained cellulose composite I was 0.41 Pa; particle L/D was 1.6; the content of the colloidal cellulose composite was 70 mass %; the median size measured by a dynamic light scattering method of the colloidal cellulose composite was 0.69 μm; the median size measured by a laser diffraction/scattering method was 0.13 μm; and the median size of coarse particles was 9.3 μm. The viscosity of a water dispersion of the cellulose composite was 75 mPa·s.

The results are shown in Table 1.

Example 7

Using chipped commercially available DP pulp, cellulose was hydrolyzed in the same manner as in Example 1. Subsequently, wet-cake like cellulose (average polymerization degree: 220) and commercially available CMC-Na (the viscosity of 2% solution: 50 mPa·s, substitution degree: 1.3) as Component B were prepared. Component A was not added. MCC and CMC-Na (Component B) were added such that the mass ratio of MCC/CMC-Na (Component B) became 90/10 (where constitution of CMC-Na: Component A/Component B=0/100), and water was added so as to obtain a solid content of 46 mass %. The mixture was kneaded in the same manner as in Example 1 to obtain cellulose composite J.

Kneading energy was controlled depending upon the kneading time of a planetary mixer, an actual value thereof was 200 Wh/kg. The kneading temperature was controlled by cooling a jacket and measured by use of a thermocouple. The mixture was kneaded at 50° C. or less until the kneading energy reached 30 Wh/kg. Thereafter, the kneaded mixture was cooled by cooling the jacket and the temperature of the kneaded mixture was 15° C. or less throughout the kneading.

The storage elastic modulus (G') of the obtained cellulose composite J was 2.6 Pa; particle L/D was 1.6; the content of the colloidal cellulose composite was 78 mass %; the median size measured by a dynamic light scattering method of the colloidal cellulose composite was 1.3 μm; the median size measured by a laser diffraction/scattering method was 0.13 μm; and the median size of coarse particles was 7.5 μm. The viscosity of a water dispersion of the cellulose composite was 180 mPa·s.

The results are shown in Table 1.

Example 8

Using chipped commercially available DP pulp, cellulose was hydrolyzed in the same manner as in Example 1. Subsequently, wet-cake like cellulose (average polymerization degree: 220), commercially available CMC-Na (the viscosity of 2% solution: 500 mPa·s, substitution degree: 1.5) as Component A, and commercially available CMC-Na (the viscosity of 2% solution: 50 mPa·s, substitution degree: 1.3) as Component B were prepared. MCC and Components A and B were added such that the mass ratio of MCC/CMC-Na (Component A+Component B) became 92/8 (where constitution of CMC-Na: Component A/Component B=25/75), and water was added so as to obtain a solid content of 48 mass %. The mixture was kneaded in the same manner as in Example 1 to obtain cellulose composite K.

Kneading energy was controlled depending upon the kneading time of a planetary mixer and an actual value thereof was 250 Wh/kg. The kneading temperature was controlled by cooling a jacket and measured by use of a thermocouple. The mixture was kneaded at 50° C. or less until the kneading energy reached 30 Wh/kg. Thereafter, the kneaded mixture was cooled by cooling the jacket and the temperature of the kneaded mixture was 40° C. or less throughout the kneading.

The storage elastic modulus (G') of the obtained cellulose composite K was 4 Pa; particle L/D was 1.6; the content of the colloidal cellulose composite was 77 mass %; the median size measured by a dynamic light scattering method of the colloidal cellulose composite was 2.2 μm; the median size measured by a laser diffraction/scattering method was 0.13 μm; and the median size of coarse particles was 7.8 μm. The viscosity of a water dispersion of the cellulose composite was 330 mPa·s.

The results are shown in Table 1.

Examples, Comparative Examples: Cocoa Beverage

Using cellulose composites A to K obtained in Examples and Comparative Examples as mentioned above, cocoa beverages were prepared by the following operation and evaluated. Previously prepared by mixing powder raw materials: cocoa powder (30 g) (a powder mixture containing an oil content of 10 mass %, sugar (50 g), whole powdered milk (8 g), table salt (0.5 g) and an emulsifier (monoglyceride preparation) (1.0 g)), and a cellulose composite (4.0 g) were added. To this mixture, ion-exchanged water warmed to 80° C. was added to obtain 1000 g. Thereafter, the mixture was stirred by a propeller (500 rpm, 10 minutes), homogenized (at 10 MPa) by a piston homogenizer and transferred to a 200 mL-volume heat-resistant glass bottle to obtain highly concentrated milk cocoa. This was subjected to heat sterilization treatment (121° C., 30 minutes) and cooled with service-water for one hour. Thereafter, the bottle container was vertically gently shaken 10 times and allowed to stand still and stored in an atmosphere of 5° C. for one month. Appearance of the bottle was visually observed. The evaluation manner was as shown below and the obtained results are shown in Table 1.

<Suspension Stability: Observation of Appearance of Food and Drink>

Various types of beverages (as to the production method, see the following Examples and Comparative Examples) were visually evaluated based on the criteria defined with respect to the following four items.

(Separation) evaluated based on the volume of an upper thin-color layer of beverage contained in a heat-resistant bottle.

⊚ (excellent): no separation, ○ (good): separation is less than 10%, Δ (acceptable): separation is less than 30%, X (unacceptable): separation is 30% or more (Sedimentation) evaluated based on the amount of deposited substance on the bottom of a heat-resistant bottle containing a beverage.

⊚ (excellent): no sedimentation, ○ (good): a partially thin sedimentation, Δ (acceptable): entirely thin sedimentation, X (unacceptable): entirely thick sedimentation (Aggregation) evaluated based on the amount of non-homogeneous portion in the entire beverage contained in a heat-resistant bottle.

⊚ (excellent): homogeneous, ○ (good): slightly partially non-homogeneous, Δ (acceptable): partially non-homogeneous, X (unacceptable): entirely non-homogeneous (Oil ring) evaluated based on the amount of ring-form solidified matter of oil along the bottle wall at upper portion of beverage contained in a heat-resistant bottle ⊚ (excellent): none, ○ (good): slightly partially formed, Δ (acceptable): incompletely ring shape formed, X (unacceptable): completely ring shape formed <Viscosity of Beverage>*The Evaluation Criteria do not Apply to Foods Except Beverages Various types of beverages (as to the production method, see the following Examples and Comparative Examples) were produced. One hour later (stored at 25° C.), each of the beverages was set in a B-type viscometer (rotor revolving speed: 60 rpm), allowed to stand still for 30 seconds and rotated for 30 seconds, and then viscosity was measured. Note that the rotor can be appropriately changed depending upon the viscosity. The rotors used herein were as follows: 1 to 20 mPa·s: BL type, 21 to 100 mPa·s: No. 1, 101 to 300 mPa·s: No. 2, 301 mPa·s: No. 3). The measurement results were classified based on the following criteria.

(Viscosity) ⊚ (excellent): 1 to 10, ○ (good): 10 to 20, Δ (acceptable): 20 to 50, X (unacceptable): 50 or more [mPa·s]

<Texture>

The evaluation criteria of texture were as follows:
⊚ (excellent): light feeling in the throat and has appropriate body.
○ (good): slightly sticky feeling in the throat.
Δ (acceptable): heavy feeling in the throat and sticky.
X (unacceptable): good feeling in the throat but watery.

<Taste: Rich Taste>

The evaluation criteria of taste were as follows:
⊚ (excellent): have satisfactory rich taste.
○ (good): have rich taste.
Δ (acceptable): have slightly rich taste.
X (unacceptable): have no rich taste.

<Viscoelasticity of Beverage: Tan δ>

Various types of beverages (as to the production method, see the following Examples and Comparative Examples) were produced. One day later of the production, beverages were backed to normal temperature (25° C.) and each of the beverages was set in a viscoelasticity measuring apparatus (ARES100FRTN1 Type, manufactured by Rheometric Scientific, Inc., geometry: Double Wall Couette type, distortion was swept in the range of 1 to 794%) to measure viscoelasticity. In the present invention, loss tangent tan δ (loss elastic modulus G"/storage elastic modulus G') was obtained from the storage elastic modulus and loss elastic modulus corresponding to a distortion of 200% on the distortion-stress curve obtained by the aforementioned measurement.

Examples, Comparative Examples: Highly Concentrated Coffee Beverage

Using cellulose composites A to K obtained in Examples and Comparative Examples as mentioned above, coffee beverages were prepared by the following operations and evaluated. Coffee powder (trade name: "Premium Blend" manufactured by Key Coffee Inc.) (250 g) was weighted on filter cloth made of cotton flannel. Boiled hot water (2000 g) was poured around the coffee powder and a coffee extract through the filter cloth was collected. The extract was subjected to measurement of Brix by a saccharimeter (trade name "PAL-1", manufactured by Atago Co., Ltd.). As a result, Brix was 3.3.

Next, to the coffee extract (64.5 parts by mass), milk (13.0 parts by mass), granulated sugar (5.0 parts by mass), an emulsifier (trade name "sucrose fatty acid ester P-1670", manufactured by Mitsubishi Kagaku Foods Corporation) (0.03 parts by mass), sodium hydrogen carbonate (special grade, manufactured by Wako Pure Chemical Industries Ltd.) (0.45 parts by mass) and each of cellulose composites A to K (0.05 parts by mass) were added. To this mixture, pure water was added to obtain a total of 100 parts by mass. Thereafter, the mixture was transferred to a 2 L-volume container made of stainless steel and stirred (300 rpm, 10 minutes) at 80° C. by a propeller. Thereafter, the dispersion solution was homogenized by a piston homogenizer (trade name: "Manton-Gaulin Homogenizer" manufactured by APV) (20 MPa). This was subjected to UHT heat sterilization treatment (140° C., 60 seconds), transferred to a 200 mL-volume heat-resistant glass bottle, closed tightly, and cooled with tap-water for one hour. Thereafter, the container (bottle) was vertically gently shaken 10 times, allowed to stand still and stored in an atmosphere of 60° C. for 28 days. Appearance of the beverage was visually observed. The evaluation manner was as follows. The obtained results are shown in Table 1.

<Suspension Stability: Observation of Appearance of Food and Drink>

Various types of beverages (as to the production method, see the following Examples and Comparative Examples) were visually evaluated based on the criteria defined with respect to the following four items.

(Separation) evaluated based on the volume of an upper thin-color layer of beverage contained in a heat-resistant bottle.

⊚ (excellent): no separation, ○ (good): separation is less than 10%, Δ (acceptable): separation is less than 30%, X (unacceptable): separation is 30% or more (Sedimentation) evaluated based on the amount of deposited substance on the bottom of a heat-resistant bottle containing a beverage.

⊚ (excellent): no sedimentation, ○ (good): a partially thin sedimentation, Δ (acceptable): entirely thin sedimentation, X (unacceptable): entirely thick sedimentation (Aggregation) evaluated based on the amount of non-homogeneous portion in the entire beverage contained in a heat-resistant bottle.

⊚ (excellent): homogeneous, ○ (good): slightly partially non-homogeneous, Δ (acceptable): partially non-homogeneous, X (unacceptable): entirely non-homogeneous (Oil ring) evaluated based on the amount of ring-form solidified matter of oil along the wall of a bottle observed at upper portion of beverage contained in a heat-resistant bottle ⊚ (excellent): none, ○ (good): slightly partially formed, Δ (acceptable): incompletely ring shape formed, X (unacceptable): completely ring shape formed <Viscosity of Beverage*The Evaluation Criteria do not Apply to Foods Except Beverages.>

Various types of beverages (as to the production method, see the following Examples and Comparative Examples) were produced. One hour later (stored at 25° C.), each of the beverages was set in a B-type viscometer (rotor revolving speed: 60 rpm), allowed to stand still for 30 seconds and rotated for 30 seconds, and then viscosity was measured. Note that the rotor can be appropriately changed depending upon the viscosity. The rotors used herein were as follows: 1 to 20 mPa·s: BL type, 21 to 100 mPa·s: No. 1, 101 to 300 mPa·s: No. 2, 301 mPa·s: No. 3). The measurement results were classified based on the following criteria.

(Viscosity) ⊚ (excellent): 1 to 10, ○ (good): 10 to 20, Δ (acceptable): 20 to 50, X (unacceptable): 50 or more [mPa·s]

<Texture>

The evaluation criteria of texture were as follows:

⊚ (excellent): light feeling in the throat and has appropriate body.

○ (good): slightly sticky feeling in the throat.

Δ (acceptable): heavy feeling in the throat and sticky.

X (unacceptable): good feeling in the throat but watery.

<Taste: Rich Taste>

The evaluation criteria of taste were as follows:

⊚ (excellent): have satisfactory rich taste.

○ (good): have rich taste.

Δ (acceptable): have slightly rich taste.

X (unacceptable): have no rich taste.

<Viscoelasticity of Beverage: Tan δ>

Various types of beverages (as to the production method, see the following Examples and Comparative Examples) were produced. One day later of the production, beverages were backed to normal temperature (25° C.) and each of the beverages was set in a viscoelasticity measuring apparatus (ARES100FRTN1 Type, manufactured by Rheometric Scientific, Inc., geometry: Double Wall Couette type, distortion was swept in the range of 1 to 794%) to measure viscoelasticity. In the present invention, loss tangent tan δ (loss elastic modulus G"/storage elastic modulus G') was obtained from the storage elastic modulus and loss elastic modulus corresponding to a distortion of 200% on the distortion-stress curve obtained by the aforementioned measurement.

Examples, Comparative Examples: Highly Concentrated Mineral Enriched Milk Beverage Using cellulose composites A to K obtained in Examples and Comparative Examples as mentioned above, highly concentrated mineral enriched milk beverages were prepared by the following operations and evaluated. Milk (20 parts by mass), fresh cream (3.2 parts by mass) and powdered skim milk (5.8 parts by mass) were added and stirred. To this mixture, dolomite ($CaMg(CO_3)_2$, density: 2.8 to 2.9 g/cm$^3$) (0.33 parts by mass), ferric pyrophosphate (0.0067 parts by mass), zinc gluconate (0.0067 parts by mass) and a cellulose composite (0.20 parts by mass) were added and further water was added to obtain a total amount of 100 parts by mass (2 L). The resultant mixture was stirred by a high-shear homogenizer (trade name "TK homogenizer MARKII" manufactured by PRIMIX Corporation) at 6000 rpm for 10 minutes. After stirring, a small amount of aqueous citric acid solution was added to adjust pH of the mixture to be 6.5. After warmed up in a warm bath of 80° C., the mixture was stirred by a propeller stirrer at 300 rpm for 10 minute and homogenized by a piston homogenizer (trade name: "Manton-Gaulin Homogenizer" manufactured by APV) (20 MPa). This was subjected to UHT heat sterilization treatment (130° C., 3 seconds), transferred to a 200 mL-volume heat-resistant glass bottle, closed tightly, and cooled with tap-water for one hour. Thereafter, the container (bottle) was vertically gently shaken 10 times and allowed to stand still and stored in an atmosphere of 5° C. for 7 days. Appearance of the beverage was visually observed. The evaluation manner is as follows. The obtained results are shown in Table 1.

<Suspension Stability: Observation of Appearance of Food and Drink>

Various types of beverages (as to the production method, see the following Examples and Comparative Examples) were visually evaluated based on the criteria defined with respect to the following four items.

(Sedimentation) evaluated based on the amount of deposited substance on the bottom of a heat-resistant bottle containing beverage.

⊚ (excellent): no sedimentation, ○ (good): partially thin sedimentation, Δ (acceptable): entirely thin sedimentation, X (unacceptable): entirely thick sedimentation (Number of re-dispersion) a beverage contained in a heat-resistant bottle was slowly and inverted upside down, the number of inversions at the time until no sedimentation was observed on the bottom was determined as the number of re-dispersion. (example: if no sedimentation was observed by upside down inverting once, the number of re-dispersion was determined as one.)

<Viscosity of Beverage*The Evaluation Criteria do not Apply to Foods Except Beverages.>

Various types of beverages (as to the production method, see the following Examples and Comparative Examples) were produced. One hour later of the production (stored at 25° C.), each of the beverages was set in a B-type viscometer (rotor revolving speed: 60 rpm), allowed to stand still for 30 seconds and rotated for 30 seconds, and then viscosity was measured. Note that the rotor can be appropriately changed depending upon the viscosity. The rotors used herein were as follows: 1 to 20 mPa·s: BL type, 21 to 100 mPa·s: No. 1, 101 to 300 mPa·s: No. 2, 301 mPa·s: No. 3). The measurement results were classified based on the following criteria.

(Viscosity) ⊚ (excellent): 1 to 10, ○ (good): 10 to 20, Δ (acceptable): 20 to 50, X (unacceptable): 50 or more [mPa·s]

<Texture>

The evaluation criteria of texture were as follows:

⊚ (excellent): light feeling in the throat and has appropriate body.

○ (good): slightly sticky feeling in the throat.

Δ (acceptable): heavy feeling in the throat and sticky.

X (unacceptable): good feeling in the throat but watery.

<Viscoelasticity of Beverage: Tan δ>

Various types of beverages (as to the production method, see the following Examples and Comparative Examples) were produced. One day later of the production, beverages were backed to normal temperature (25° C.) and each of the beverages was set in a viscoelasticity measuring apparatus (ARES100FRTN1 Type, manufactured by Rheometric Scientific, Inc., geometry: Double Wall Couette type, distortion was swept in the range of 1 to 794%) to measure viscoelasticity. In the present invention, loss tangent tan δ (loss elastic modulus G"/storage elastic modulus G') was obtained from the storage elastic modulus and loss elastic modulus corresponding to a distortion of 200% on the distortion-stress curve obtained by the aforementioned measurement.

Examples, Comparative Examples: Black-Sesame Containing Milk Beverage

Using cellulose composites A to K obtained in Examples and Comparative Examples as mentioned above, black-sesame containing milk beverages were prepared by the following operations and evaluated. To a mixture of Oats powder (30 g) (density 1.0 to 1.5 g/cm$^3$), sesame paste (30 g), granulated sugar (70 g), skim milk (manufactured by Snow Brand Milk Products Co., Ltd.) (10 g), peanut butter (manufactured by MEIDI-YA) (10 g), malt extract (5 g), glyceryl monostearate (manufactured by Wako Pure Chemical Industries Ltd.) (1.5 g) and water (842 g), each of cellulose composites A to K (1.5 g) was blended and a beverage was prepared by the following procedures. First, powder components mentioned above except water were mixed (manually shaken for three minutes in a PE bag) and then added the obtained mixture to water of 80° C. The mixture was dispersed by use of a high-shear homogenizer (trade name "TK homogenizing mixer MARKII Model 2.5" manufactured by PRIMIX Corporation, treatment conditions: rotation number 7,000 rpm×5 minutes, total amount 1000 g). Subsequently, the mixture was passed once through a colloid mill (trade name "MC-1" manufactured by SMT CO., LTD.) and again heated to 70° C. Thereafter, the mixture was homogenized by a piston homogenizer (trade name: "Manton-Gaulin Homogenizer" manufactured by APV) (20 MPa), subjected to UHT sterilization treatment (140° C., 30 seconds), transferred to a 250 mL-volume heat-resistant glass bottle, closed tightly, stored at 5° C. for one day and evaluated as follows. The results are shown in Table 1.

<Suspension Stability: Observation of Appearance of Food and Drink>

Various types of beverages (as to the production method, see the following Examples and Comparative Examples) were visually evaluated based on the criteria defined with respect to the following four items.

(Separation) evaluated based on the volume of an upper thin-color layer of beverage contained in a heat-resistant bottle.

⊚ (excellent): no separation, ○ (good): separation is less than 10%, Δ (acceptable): separation is less than 30%, X (unacceptable): separation is 30% or more (Sedimentation) The heat-resistant bottle was slowly and upside down inverted and sedimentation was evaluated based on the amount of deposited substance on the bottom.

⊚ (excellent): no deposition, ○ (good): partially thin deposition, Δ (acceptable): entirely thin deposition, X (unacceptable): entirely thick deposition (Aggregation) evaluated based on the amount of non-homogeneous portion in the entire beverage contained in a heat-resistant bottle.

⊚ (excellent): homogeneous, ○ (good): slightly partially non-homogeneous, Δ (acceptable): partially non-homogeneous, X (unacceptable): entirely non-homogeneous <Texture>

The evaluation criteria of texture were as follows:

⊚ (excellent): light feeling in the throat and has appropriate body.

○ (good): slightly sticky feeling in the throat.

Δ (acceptable): heavy feeling in the throat and sticky.

X (unacceptable): good feeling in the throat but watery.

Examples, Comparative Examples: Azuki Bean-Containing Milk Beverage

Using cellulose composites A to K obtained in Examples and Comparative Examples as mentioned above, Azuki bean-containing milk beverages were prepared by the following operations and evaluated. To dry Azuki beans (75 g), water (1287 g) was added. The mixture was allowed to stand still at normal temperature for 4 hours and boiled for 1.5 hours. After the mixture was cooled to 70° C., it was passed once through a colloid mill in the same manner as above. The treated dispersion solution was passed through a sieve made of SUS and having 40 meshes. After this operation was repeated twice, a powder mixture, which was previously prepared by blending powder milk (Brite C-40, manufactured by Nestle) (15 g), granulated sugar (120 g), glyceryl monostearate (manufactured by Wako Pure Chemical Industries Ltd.) (1.5 g) and a cellulose composite (1.5 g), was added. The resultant mixture was treated by the aforementioned TK homogenizer at 7000 rpm for 5 minutes, homogenized by the aforementioned piston homogenizer (trade name: "Manton-Gaulin Homogenizer" manufactured by APV) (20 MPa), subjected to UHT sterilization treatment (140° C., 30 seconds), transferred to a 250 mL-volume heat-resistant glass bottle, closed tightly, stored at 5° C. for one day and evaluated as follows. The results are shown in Table 1.

<Suspension Stability: Observation of Appearance of Food and Drink>

Various types of beverages (as to the production method, see the following Examples and Comparative Examples) were visually evaluated based on the criteria defined with respect to the following four items.

(Separation) evaluated based on the volume of an upper thin-color layer of beverage contained in a heat-resistant bottle.

⊚ (excellent): no separation, ○ (good): separation is less than 10%, Δ (acceptable): separation is less than 30%, X (unacceptable): separation is 30% or more (Sedimentation) The heat-resistant bottle was slowly and upside down inverted and sedimentation was evaluated based on the amount of deposited substance on the bottom.

⊚ (excellent): no deposition, ○ (good): partially thin deposition, Δ (acceptable): entirely thin deposition, X (unacceptable): entirely thick deposition (Aggregation) evaluated based on the amount of non-homogeneous portion in the entire beverage contained in a heat-resistant bottle.

⊚ (excellent): homogeneous, ○ (good): slightly partially non-homogeneous, Δ (acceptable): partially non-homogeneous, X (unacceptable): entirely non-homogeneous <Texture>

The evaluation criteria of texture were as follows:

⊚ (excellent): light feeling in the throat and has appropriate body.

○ (good): slightly sticky feeling in the throat.

Δ (acceptable): heavy feeling in the throat and sticky.

X (unacceptable): good feeling in the throat but watery.

<Color Fading after Sterilization>

Color fading was evaluated based on the following criteria.

⊚ (excellent): no color fading is observed in comparison between before and after sterilization.

○ (good): color fading is slightly observed in comparison between before and after sterilization.

Δ (acceptable): color fading is somewhat observed in comparison between before and after sterilization.

X (unacceptable): color fading is clearly observed in comparison between before and after sterilization.

TABLE 1

| | | Example 1 | Example 2 | Example 3 | Example 4 | Example 5 | Example 6 | Example 7 | Example 8 | Comparative Example 1 | Comparative Example 2 | Comparative Example 3 |
|---|---|---|---|---|---|---|---|---|---|---|---|---|
| | | A | B | C | D | E | F | J | K | G | H | I |
| Composition (mass %) | Cellulose composite | | | | | | | | | | | |
| | Cellulose | 90 | 52 | 80 | 90 | 70 | 90 | 90 | 92 | 90 | 80 | 90 |
| | CMC-Na | 10 | 48 | 20 | 10 | 5 | 10 | 10 | 8 | 10 | 20 | 10 |
| | Xanthan gum | — | — | — | — | 5 | — | — | — | — | — | — |
| | Dextrin | — | — | — | — | 20 | — | — | — | — | — | — |
| Constitution of CMC-Na | Viscosity of Component A (mPa·s) | 620 | 7000 | 620 | 620 | 620 | — | — | — | 620 | — | — |
| | Viscosity of Component B (mPa·s) | 25 | 25 | 25 | 25 | 25 | — | — | 500 | — | — | — |
| | Blending ratio of Component A (mass ratio) | 50 | 10 | 40 | 25 | 25 | — | 50 | 25 | 100 | — | — |
| | Blending ratio of Component B (mass ratio) | 50 | 90 | 60 | 60 | 50 | 25 | — | 25 | — | — | — |
| Composite formation condition | Solid content (mass %) | 45 | 45 | 40 | 50 | 50 | 45 | 46 | 75 | 37 | 11 | 40 |
| | Kneading energy (Wh/kg) | 390 | 220 | 190 | 100 | 80 | 200 | 200 | 48 | 60 | 30 | 60 |
| | Kneading temperature (°C.) | About 40 | About 40 | About 60 | About 65 | About 65 | About 15 | About 15 | About 40 | About 85 | About 60 | About 85 |
| Basic physical properties of composite | Average polymerization degree of cellulose | 220 | 220 | 220 | 220 | 220 | 220 | 220 | 220 | 220 | 200 | 220 |
| | Cellulose particle L/D | 1.6 | 1.6 | 1.6 | 1.6 | 1.6 | 1.6 | 1.6 | 1.6 | 1.6 | 1.3 | 1.6 |
| | G' of composite (Pa) | 5.5 | 1.4 | 2.3 | 2.5 | 1.2 | 1.0 | 2.6 | 4 | 0.45 | 0.38 | 0.41 |
| | Content of colloidal cellulose composite (mass ratio) | 78 | 69 | 67 | 72 | 75 | 78 | 78 | 77 | 70 | 91 | 70 |
| | Median size by a dynamic light scattering method (μm) | 2.5 | 1.2 | 1.1 | 1.2 | 0.95 | 0.85 | 1.3 | 2.2 | 0.81 | 0.65 | 0.69 |
| | Median size by laser diffraction (μm) | 0.13 | 0.13 | 0.13 | 0.13 | 0.16 | 0.13 | 0.13 | 0.13 | 0.13 | 0.11 | 0.13 |
| | Median size of coarse particles (μm) | 6.5 | 9.3 | 8.2 | 9.1 | 8.5 | 7.8 | 7.5 | 7.8 | 9.5 | 3.4 | 9.3 |
| | Viscosity of water dispersion of cellulose composite (mPa·s) | 383 | 252 | 182 | 220 | 140 | 175 | 180 | 330 | 98 | 80 | 75 |
| Evaluation results of cocoa beverage | Separation | ○ | ⊚ | ⊚ | ⊚ | ⊚ | ○ | ⊚ | ⊚ | ○ | ○ | ○ |
| | Sedimentation | ⊚ | ⊚ | ○ | ○ | ⊚ | △ | ○ | ⊚ | × | △ | × |
| | Aggregation | ○ | ○ | ○ | ○ | ⊚ | ○ | ⊚ | ⊚ | ○ | △ | ○ |
| | Oil ring | ⊚ | ⊚ | ⊚ | ⊚ | ⊚ | ⊚ | ⊚ | ⊚ | × | × | × |
| | Viscosity | ○ | ⊚ | ⊚ | ⊚ | ⊚ | ⊚ | ⊚ | ⊚ | ⊚ | ⊚ | ⊚ |

TABLE 1-continued

| | | Example 1 | Example 2 | Example 3 | Example 4 | Example 5 | Example 6 | Example 7 | Example 8 | Comparative Example 1 | Comparative Example 2 | Comparative Example 3 |
|---|---|---|---|---|---|---|---|---|---|---|---|---|
| Evaluation results of coffee beverage | Texture (easy-to-drink) | ○ | ◎ | ◎ | ◎ | ◎ | ◎ | ◎ | ◎ | X | X | X |
| | Viscoelasticity, tan δ | 1.9 | 1.5 | 1.4 | 1.7 | 1.4 | 1.2 | 1.7 | 1.8 | 0.9 | 0.8 | 0.9 |
| | Rich taste of beverage | ◎ | ◎ | ◎ | ◎ | ◎ | ◎ | ◎ | ◎ | △ | X | △ |
| | Separation | ◎ | ◎ | ◎ | ◎ | ◎ | ○ | ◎ | ◎ | ◎ | ◎ | ◎ |
| | Sedimentation | ◎ | ○ | ○ | ◎ | ○ | ○ | ◎ | ◎ | △ | X | X |
| | Aggregation | ○ | ◎ | ◎ | ◎ | ◎ | △ | ◎ | ◎ | X | X | X |
| | Oil ring | ◎ | ◎ | ◎ | ◎ | ◎ | ○ | ◎ | ◎ | X | X | X |
| | Viscosity | ◎ | ◎ | ◎ | ◎ | ◎ | ◎ | ◎ | ◎ | ◎ | ◎ | ◎ |
| Evaluation results of milk beverage | Texture (easy-to-drink) | ◎ | ◎ | ◎ | ◎ | ◎ | ◎ | ◎ | ◎ | △ | X | △ |
| | Viscoelasticity, tan δ | 1.8 | 1.4 | 1.4 | 1.6 | 1.3 | 1.1 | 1.7 | 1.8 | 0.8 | 0.8 | 0.8 |
| | Rich taste of beverage | ◎ | ◎ | ◎ | ◎ | ◎ | ◎ | ◎ | ◎ | △ | X | △ |
| | Sedimentation | ○ | ○ | ○ | ○ | ○ | △ | ○ | ◎ | X | X | X |
| | Re-dispersion times | 1 | 2 | 2 | 1 | 3 | 3 | 1 | 0 | 8 | 10 | 8 |
| | Viscosity | ◎ | ◎ | ◎ | ◎ | ◎ | ◎ | ◎ | ◎ | ◎ | ◎ | ◎ |
| Evaluation results of black sesame beverage | Texture (easy-to-drink) | ○ | ◎ | ◎ | ◎ | ◎ | ◎ | ◎ | ◎ | X | X | X |
| | Viscoelasticity, tan δ | 1.9 | 1.4 | 1.4 | 1.6 | 1.4 | 1.2 | 1.7 | 1.8 | 0.8 | 0.8 | 0.9 |
| | Separation | ◎ | ◎ | ◎ | ◎ | ◎ | ◎ | ◎ | ◎ | X | X | X |
| | Sedimentation | ○ | ○ | ○ | ○ | ○ | ○ | ◎ | ◎ | ○ | ○ | ○ |
| | Aggregation | ◎ | ◎ | ◎ | ◎ | ◎ | ◎ | ◎ | ◎ | ◎ | ◎ | ◎ |
| Evaluation results of Azuki beverage | Texture (easy-to-drink) | ◎ | ◎ | ◎ | ◎ | ◎ | ◎ | ◎ | ◎ | X | X | X |
| | Separation | ○ | ○ | ○ | ○ | ○ | ○ | ◎ | ◎ | ○ | ○ | ○ |
| | Sedimentation | ◎ | ◎ | ◎ | ◎ | ◎ | ◎ | ◎ | ◎ | ◎ | ◎ | ◎ |
| | Aggregation | ○ | ○ | ○ | ○ | ○ | ○ | ◎ | ◎ | ○ | ○ | ○ |
| | Texture (easy-to-drink) | ◎ | ◎ | ◎ | ◎ | ◎ | ◎ | ◎ | ◎ | △ | △ | △ |
| | Color fading after sterilization | | | | | | | | | | | |

INDUSTRIAL APPLICABILITY

Owing to addition of the cellulose composite of the present invention to a food and drink, occurrence of separation, aggregation and sedimentation of a component can be suppressed and a suspension can be stabilized. Furthermore, since the cellulose composite of the present invention is excellent in suspension stability, it is useful for use in rich taste beverages containing a component such as cocoa, coffee, tea and milk in a high concentration. Furthermore, the cellulose composite of the present invention is useful since it exhibits excellent suspension stability in foods and drinks containing a water-insoluble component such as a functional food material in these beverages. Furthermore, the cellulose composite of the present invention is also useful for medicinal products and industrial products.

The invention claimed is:

1. A method for producing a cellulose composite comprising:
    treating a mixture containing cellulose, a polysaccharide and an aqueous medium together in a wet process, wherein a solid content is controlled to be 35 mass % or more, and temperature is set at 80° C. or less to obtain the cellulose composite comprising colloidal cellulose composites comprising the cellulose and the polysaccharide and having a median size of at least 0.85 µm, the median size determined from:
    1) suspending the cellulose composite in pure water at 0.5 mass % to obtain a suspension,
    2) homogenizing the suspension with a high-shear auto homogenizer at 15000 rpm for 5 minutes to obtain a homogenized suspension,
    3) centrifuging the homogenized suspension in a first centrifugation at 39200 m$^2$/s for 10 minutes to obtain a first supernatant and a first precipitate,
    4) separating the first supernatant from the first precipitate,
    5) centrifuging the first supernatant in a second centrifugation at 116000 m$^2$/s for 45 minutes to obtain a second supernatant and a second precipitate,
    6) separating the second supernatant from the second precipitate,
    7) ultra-sonicating the second supernatant for 10 minutes to obtain a product of the ultra-sonication, and
    8) determining the median size of the colloidal cellulose composites from the product of the ultra-sonication by a zeta potential-particle size dynamic light scattering system, the median size of the colloidal cellulose composites being a cumulative 50% scattering intensity in a frequency distribution measured by the zeta potential-particle size dynamic light scattering measurement system.

2. The method for producing the cellulose composite according to claim 1, wherein the polysaccharide is sodium carboxymethylcellulose and the sodium carboxymethylcellulose has a molecular-weight distribution, which is obtained by gel permeation chromatography performed in a 0.05 M sodium hydroxide, having two (bimodal) peaks or more.

3. The method for producing the cellulose composite according to claim 1, wherein the polysaccharide is sodium carboxymethylcellulose and the sodium carboxymethylcellulose contains Component A having a viscosity of 100 mPa·s or more and Component B having a viscosity of less than 100 mPa·s in a mass ratio of 5/95 to 95/5.

4. The method for producing the cellulose composite according to claim 2, wherein the sodium carboxymethylcellulose has a substitution degree of 1 or more.

5. A food, a drink, a medicinal product, or an industrial product containing a cellulose composite and a water-insoluble component in an aqueous medium and having a loss tangent, tan δ (loss elastic modulus G"/storage elastic modulus G') of 1.5 or more, the cellulose composite comprising colloidal cellulose composites comprising cellulose and polysaccharide and having a median size of at least 0.85 µm, the median size determined from:
    1) suspending the cellulose composite in pure water at 0.5 mass % to obtain a suspension,
    2) homogenizing the suspension with a high-shear auto homogenizer at 15000 rpm for 5 minutes to obtain a homogenized suspension,
    3) centrifuging the homogenized suspension in a first centrifugation at 39200 m$^2$/s for 10 minutes to obtain a first supernatant and a first precipitate,
    4) separating the first supernatant from the first precipitate,
    5) centrifuging the first supernatant in a second centrifugation at 116000 m$^2$/s for 45 minutes to obtain a second supernatant and a second precipitate,
    6) separating the second supernatant from the second precipitate,
    7) ultra-sonicating the second supernatant for 10 minutes to obtain a product of the ultra-sonication, and
    8) determining the median size of the colloidal cellulose composites from the product of the ultra-sonication by a zeta potential-particle size dynamic light scattering system, the median size of the colloidal cellulose composites being a cumulative 50% scattering intensity in a frequency distribution measured by the zeta potential-particle size dynamic light scattering measurement system.

* * * * *